(12) United States Patent
Amarasinghe et al.

(10) Patent No.: US 8,013,161 B1
(45) Date of Patent: Sep. 6, 2011

(54) FLUOROALKYL TETRABENAZINE CARBINOL COMPOUNDS AS IMAGING AGENTS AND PROBES

(75) Inventors: Kande Kankanamalage Dayarathna Amarasinghe, Latham, NY (US); Michael James Rishel, Rensselaer, NY (US); Sean Richard Dinn, Delmar, NY (US); Bruce Fletcher Johnson, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 941 days.

(21) Appl. No.: 11/952,325

(22) Filed: Dec. 7, 2007

(51) Int. Cl.
*C07D 455/06* (2006.01)

(52) U.S. Cl. ....................................... 546/95

(58) Field of Classification Search ............... 546/95
See application file for complete search history.

(56) References Cited

U.S. PATENT DOCUMENTS

| | | | |
|---|---|---|---|
| 2,843,591 | A | 7/1958 | Brossi et al. |
| 4,193,998 | A | 3/1980 | Szantay et al. |
| 5,278,308 | A | 1/1994 | Kung |
| 7,919,622 | B2 * | 4/2011 | Amarasinghe et al. ......... 546/95 |

FOREIGN PATENT DOCUMENTS

| | | |
|---|---|---|
| DE | 1068261 B1 | 11/1959 |
| WO | W09316730 A1 | 9/1993 |
| WO | W02005077946 A1 | 8/2005 |
| WO | 2007005283 A2 | 1/2007 |
| WO | 2007130365 A2 | 11/2007 |
| WO | W02008154243 A1 | 12/2008 |

OTHER PUBLICATIONS

Popp et al., "Synthesis of Potential Antineoplastic Agents XXVI: 1,3,4,6,7,11b-Hexahydro-9,10-dimethoxy-2H-benso[a]2-quinolizinone Derivatives", Journal of Pharmaceutical Sciences, vol. 67, No. 6, pp. 871-873, XP-002513807, Jun. 1978.
PCT International Search Report dated Feb. 18, 2009.
PCT International Search Report dated Apr. 3, 2009.
Zheng et al., "Computational Neural Network Analysis of the Affinity of Lobeline and Tetrabenazine Analogs for the Vesicular Monoamine Transporter-2", Bioorganic & Medicinal Chemistry, vol. 15, pp. 2975-2992, 2007.
Kung et al., "Characterization of Optically Resolved 9-Fluoropropyl-Dihydrotetrabenzaine as a Potential PET Imaging Agent Targeting Vesicular Monoamine Transporters", Nuclear Medicine and Biology, vol. 34, pp. 239-246, 2007.
Goswami et al., "Fluoroalkyl Derivatives of Dihydrotetrabenazine as Positron Emission Tomography Imaging Agents Targeting Vesicular Monoamine Transporters", Nuclear Medicine and Biology, vol. 33, pp. 685-694, 2006.
Kilbourn et al., "Pharmacokinetics of [18F]Fluoroalkyl Derivatives of Dihydrotetrabenazine in Rate and Monkey Brain", Nuclear Medicine and Biology, vol. 34, pp. 233-237, 2007.
Kande Kankanamalage Dayarathna Amarasinghe et al.; Intermediates for Fluorinated Tetrabenazine Carbinol Compounds Imaging Agents and Probes; Filed Herewith.

* cited by examiner

*Primary Examiner* — Nizal Chandrakumar
(74) *Attorney, Agent, or Firm* — Andrew J. Caruso

(57) ABSTRACT

The present invention provides novel fluoroalkyl tetrabenazine carbinol compounds having structure I

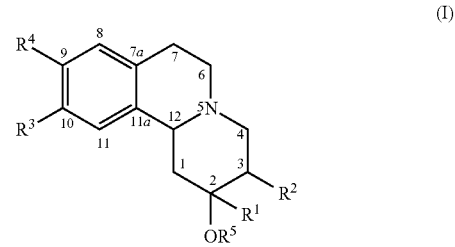

(I)

wherein $R^1$ is a $C_1$-$C_{10}$ fluorinated aliphatic radical; $R^2$ is a $C_1$-$C_{10}$ aliphatic radical; $R^3$ is hydrogen or a $C_1$-$C_{10}$ aliphatic radical; $R^4$ is hydrogen or a $C_1$-$C_{10}$ aliphatic radical; and $R^5$ is hydrogen, a $C_1$-$C_{10}$ aliphatic radical, a $C_2$-$C_{10}$ cycloaliphatic radical, or a $C_2$-$C_{20}$ aromatic radical. In a particular embodiment, —$OR^5$ is an ester moiety. The fluoroalkyl tetrabenazine carbinol compounds are provided in both racemic and enantiomerically enriched forms and may comprise either or both of fluorine-18 and fluorine 19. The fluoroalkyl tetrabenazine carbinol compounds are shown to possess high affinity for VMAT-2, a biomarker implicated in human diabetes. The fluoroalkyl tetrabenazine carbinol compounds comprising a fluorine-18 group are useful as PET imaging agents targeting the VMAT-2 biomarker. The non-radiolabled fluoroalkyl tetrabenazine carbinol compounds are useful as probes for the discovery of PET imaging agents.

25 Claims, No Drawings

FLUOROALKYL TETRABENAZINE CARBINOL COMPOUNDS AS IMAGING AGENTS AND PROBES

CROSS REFERENCE TO RELATED APPLICATIONS

This application is related to U.S. patent application Ser. Nos. 11/760,359, and 11/760,372 filed Jun. 8, 2007, U.S. patent application Ser. Nos. 11/923,926 and 11/923,805 filed Oct. 25, 2007, and U.S. patent application Ser. Nos. 11/947,215 and 11/947,275 filed Nov. 29, 2007.

BACKGROUND

This invention relates to carbinol compounds related to tetrabenazine and intermediates useful in the preparation of such fluoroalkyl tetrabenazine carbinol compounds Since first reported on in 1957 (Pletscher, A. (1957) Release of 5-hydroxytryptamine by benzoquinolizine derivatives with sedative action, *Science* 126, 507), tetrabenazine and structurally related compounds have been widely investigated, and a number of tetrabenazine (TBZ) compounds and derivatives of tetrabenazine have shown promise in the treatment of a variety of conditions affecting human health. For example, dihydrotetrabenazine has been identified as an agent for the treatment of schizophrenia and other psychoses (See for example WO 2007017654 A1), and tetrabenazine has shown promise as an agent in the treatment of Huntington's disease (Neurology (2006), 66(3), 366-372). Although most preparations used in biological studies of tetrabenazine and its derivatives have been carried out on racemates, in at least one instance the biological activity exhibited by enantiomers tested separately was highly differentiated (See Koeppe, R. A. et al. (1999) Assessment of extrastriatal vesicular monoamine transporter binding site density using stereoisomers of [11C] dihydrotetrabenazine, *J Cereb Blood Flow Metab* 19, 1376-1384).

More recently, derivatives of 9-desmethyl (±)-dihydrotetrabenazine incorporating a fluorine-18 atom have been shown to be useful as PET imaging agents, *Nuclear Medicine and Biology* 33 (2006) 685-694. See also *Nuclear Medicine and Biology* 34 (2007) 239-246; and *Nuclear Medicine and Biology* 34 (2007) 233-237.

The present invention provides both a new class of fluorinated tetrabenazine derivatives and fluorinated tetrabenazine analogs, and discloses efficient synthetic methodology, which may be used to prepare such compounds in enantiomerically enriched or racemic forms. The fluoroalkyl tetrabenazine carbinol compounds provided by the present invention are useful as PET imaging agents, probes for the development of PET imaging agents, and therapeutic agents. In addition, the present invention provides novel synthetic intermediate compositions, which may be used to prepare either or both enantiomers of the subject tetrabenazine derivatives.

BRIEF DESCRIPTION

In one embodiment, the present invention provides a fluoroalkyl tetrabenazine carbinol compound having structure I

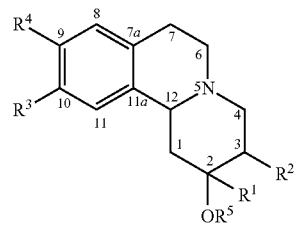

wherein $R^1$ is a $C_1$-$C_{10}$ fluorinated aliphatic radical; $R^2$ is a $C_1$-$C_{10}$ aliphatic radical; $R^3$ is hydrogen or a $C_1$-$C_{10}$ aliphatic radical; $R^4$ is hydrogen or a $C_1$-$C_{10}$ aliphatic radical; and $R^5$ is hydrogen, a $C_1$-$C_{10}$ aliphatic radical, a $C_2$-$C_{10}$ cycloaliphatic radical, or a $C_2$-$C_{20}$ aromatic radical.

In another embodiment, the prsent invention provides a PET imaging agent comprising a fluoroalkyl tetrabenazine carbinol compounds having structure I

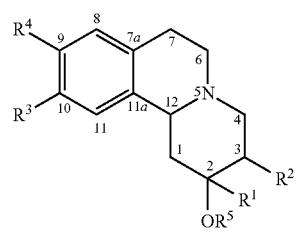

wherein $R^1$ is a $C_1$-$C_{10}$ fluorinated aliphatic radical comprising at least one fluorine-18 atom; $R^2$ is a $C_1$-$C_{10}$ aliphatic radical; $R^3$ is hydrogen or a $C_1$-$C_{10}$ aliphatic radical; $R^4$ is hydrogen or a $C_1$-$C_{10}$ aliphatic radical; and $R^5$ is hydrogen, a $C_1$-$C_{10}$ aliphatic radical, a $C_2$-$C_{10}$ cycloaliphatic radical, or a $C_2$-$C_{20}$ aromatic radical.

In yet another embodiment, the present invention provides fluoroalkyl tetrabenazine carbinol compounds having structure IV

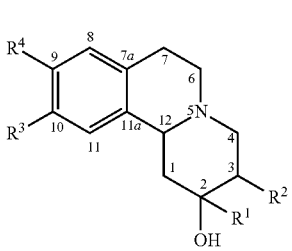

wherein $R^1$ is a $C_1$-$C_{10}$ fluorinated aliphatic radical; $R^2$ is a $C_1$-$C_{10}$ aliphatic radical; $R^3$ is hydrogen or a $C_1$-$C_{10}$ aliphatic radical; and $R^4$ is hydrogen or a $C_1$-$C_{10}$ aliphatic radical.

In yet another embodiment, the present invention provides a PET imaging agent comprising a fluoroalkyl tetrabenazine carbinol compounds having structure IV

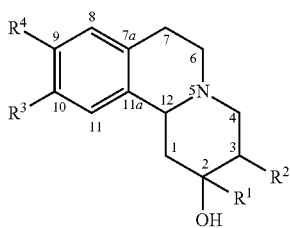

(IV)

wherein $R^1$ is a $C_1$-$C_{10}$ fluorinated aliphatic radical; $R^2$ is a $C_1$-$C_{10}$ aliphatic radical; $R^3$ is hydrogen or a $C_1$-$C_{10}$ aliphatic radical; and $R^4$ is hydrogen or a $C_1$-$C_{10}$ aliphatic radical.

DETAILED DESCRIPTION

In the following specification and the claims, which follow, reference will be made to a number of terms, which shall be defined to have the following meanings The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein, the term "solvent" can refer to a single solvent or a mixture of solvents.

Approximating language, as used herein throughout the specification and claims, may be applied to modify any quantitative representation that could permissibly vary without resulting in a change in the basic function to which it is related. Accordingly, a value modified by a term or terms, such as "about", is not to be limited to the precise value specified. In some instances, the approximating language may correspond to the precision of an instrument for measuring the value.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include nonaromatic components. For example, a benzyl group is an aromatic radical, which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —OPhC(CF$_3$)$_2$PhO—), 4-chloromethylphen-1-yl, 3-trifluorovinyl-2-thienyl, 3-trichloromethylphen-1-yl (i.e., 3-CCl$_3$Ph-), 4-(3-bromoprop-1-yl)phen-1-yl (i.e., 4-BrCH$_2$CH$_2$CH$_2$Ph-), and the like. Further examples of aromatic radicals include 4-allyloxyphen-1-oxy, 4-aminophen-1-yl (i.e., 4-H$_2$NPh-), 3-aminocarbonylphen-1-yl (i.e., NH$_2$COPh-), 4-benzoylphen-1-yl, dicyanomethylidenebis(4-phen-1-yloxy) (i.e., OPhC(CN)$_2$PhO—), 3-methylphen-1-yl, methylenebis(4-phen-1-yloxy) (i.e., —OPhCH$_2$PhO—), 2-ethylphen-1-yl, phenylethenyl, 3-formyl-2-thienyl, 2-hexyl-5-furanyl, hexamethylene-1,6-bis(4-phen-1-yloxy) (i.e., —OPh(CH$_2$)$_6$PhO—), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-CH$_3$SPh-), 3-methoxyphen-1-yl, 2-methoxycarbonylphen-1-yloxy (e.g., methyl salicyl), 2-nitromethylphen-1-yl (i.e., 2-NO$_2$CH$_2$Ph), 3-trimethylsilylphen-1-yl, 4-t-butyldimethylsilylphenl-1-yl, 4-vinylphen-1-yl, vinylidenebis (phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is a cycloaliphatic radical, which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., —$C_6H_{10}C(CF_3)_2C_6H_{10}$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g., $CH_3CHBrCH_2C_6H_{10}O$—), and the like. Further examples of cycloaliphatic radicals include 4-allyloxycyclohex-1-yl, 4-aminocyclohex-1-yl (i.e., H₂C₆H₁₀—), 4-aminocarbonyl-cyclopent-1-yl (i.e., NH₂COC₅H₈—), 4-acetyloxycyclohex-1-yl, 2,2-dicyanoisopropylidenebis(cyclohex-4-yloxy) (i.e., —OC₆H₁₀C(CN)₂C₆H₁₀O—), 3-methylcyclohex-1-yl, methylenebis(cyclohex-4-yloxy) (i.e., —OC₆H₁₀CH₂C₆H₁₀O—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —OC₆H₁₀(CH₂)₆C₆H₁₀O—), 4-hydroxymethylcyclohex-1-yl (i.e., 4-HOCH₂C₆H₁₀—), 4-mercaptomethylcyclohex-1-yl (i.e., 4-HSCH₂C₆H₁₀—), 4-methylthiocyclohex-1-yl (i.e., 4-CH₃SC₆H₁₀—), 4-methoxycyclohex-1-yl, 2-methoxycarbonylcyclohex-1-yloxy (2-CH₃OCOC₆H₁₀O—), 4-nitromethylcyclohex-1-yl (i.e., NO₂CH₂C₆H₁₀—), 3-trimethylsilylcyclohex-1-yl, 2-t-butyldimethylsilylcyclopent-1-yl, 4-trimethoxysilylethylcyclohex-1-yl (e.g., (CH₃O)₃SiCH₂CH₂C₆H₁₀—), 4-vinylcyclohexen-1-yl, vinylidenebis (cyclohexyl), and the like. The term "a C₃-C₁₀ cycloaliphatic radical" includes cycloaliphatic radicals containing at least three but no more than 10 carbon atoms. The cycloaliphatic radical 2-tetrahydrofuranyl (C₄H₇O—) represents a C₄ cycloaliphatic radical. The cyclohexylmethyl radical (C₆H₁₁CH₂—) represents a C₇ cycloaliphatic radical.

As used herein the term "aliphatic radical" refers to an organic radical having a valence of at least one consisting of a linear or branched array of atoms, which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a C₆ aliphatic radical comprising a methyl group, the methyl group being a functional group which is an alkyl group. Similarly, the 4-nitrobut-1-yl group is a C₄ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —CH₂CHBrCH₂—), and the like. Further examples of aliphatic radicals include allyl, aminocarbonyl (i.e., —CONH₂), carbonyl, 2,2-dicyanoisopropylidene (i.e., —CH₂C(CN)₂CH₂—), methyl (i.e., —CH₃), methylene (i.e., —CH₂—), ethyl, ethylene, formyl (i.e., —CHO), hexyl, hexamethylene, hydroxymethyl (i.e., —CH₂OH), mercaptomethyl (i.e., —CH₂SH), methylthio (i.e., —SCH₃), methylthiomethyl (i.e., —CH₂SCH₃), methoxy, methoxycarbonyl (i.e., CH₃OCO—), nitromethyl (i.e., —CH₂NO₂), thiocarbonyl, trimethylsilyl (i.e., (CH₃)₃Si—), t-butyldimethylsilyl, 3-trimethyoxysilylpropyl (i.e., (CH₃O)₃SiCH₂CH₂CH₂—), vinyl, vinylidene, and the like. By way of further example, a C₁-C₁₀ aliphatic radical contains at least one but no more than 10 carbon atoms. A methyl group (i.e., CH₃—) is an example of a C₁ aliphatic radical. A decyl group (i.e., CH₃(CH₂)₉—) is an example of a C₁₀ aliphatic radical.

As noted, in one embodiment the present invention provides a fluoroalkyl tetrabenazine carbinol compound having structure I

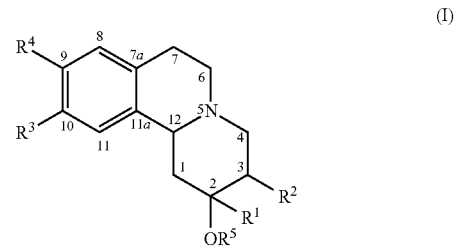

wherein $R^1$ is a $C_1$-$C_{10}$ fluorinated aliphatic radical; $R^2$ is a $C_1$-$C_{10}$ aliphatic radical; $R^3$ is hydrogen or a $C_1$-$C_{10}$ aliphatic radical; $R^4$ is hydrogen or a $C_1$-$C_{10}$ aliphatic radical; and $R^5$ is hydrogen, a $C_1$-$C_{10}$ aliphatic radical, a $C_2$-$C_{10}$ cycloaliphatic radical, or a $C_2$-$C_{20}$ aromatic radical.

As noted, in another embodiment the present invention provides a fluoroalkyl tetrabenazine carbinol compound having structure IV

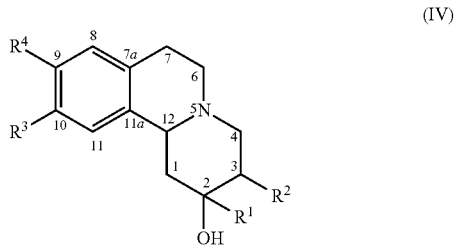

wherein $R^1$ is a $C_1$-$C_{10}$ fluorinated aliphatic radical; $R^2$ is a $C_1$-$C_{10}$ aliphatic radical; $R^3$ is hydrogen or a $C_1$-$C_{10}$ aliphatic radical; and $R^4$ is hydrogen or a $C_1$-$C_{10}$ aliphatic radical.

Those skilled in the art will appreciate that the term "fluoroalkyl tetrabenazine carbinol compound" refers to compounds falling within the scope of generic structure I and includes compounds in which $R^5$ is hydrogen (fluoroalkyl tetrabenazine compounds having a tertiary hydroxy group at ring position-2), as well as compounds in which $R^5$ is a $C_1$-$C_{10}$ aliphatic radical, a $C_2$-$C_{10}$ cycloaliphatic radical, or a $C_2$-$C_{20}$ aromatic radical (fluoroalkyl tetrabenazine carbinol compounds incorporating a derivative of a tertiary hydroxy group at ring position-2). For convenience, compounds defined by generic structure I are referred to at times herein as "tetrabenazine carbinol compounds".

The fluoroalkyl tetrabenazine carbinol compounds provided by the present invention are shown herein to possess a high affinity for Type 2 Vesicular Monoamine Transporters (VMAT-2), a group of biomarkers, which correlate with diabetic activity in human patients. The discovery that substitution at ring position-2 of the tetrabenazine structure by an aliphatic radical comprising a fluorine atom is tolerated with respect to VMAT-2 binding in this series of novel fluoroalkyl tetrabenazine carbinol compounds enables the compounds of present invention to be used as positron emission tomography (PET) imaging agents in studies targeting the VMAT-2 biomarker.

Thus, in one embodiment, the present invention provides radiolabeled fluoroalkyl tetrabenazine carbinol compounds falling within the scope of generic structure I comprising a fluorine-18 atom. In an alternate embodiment, the present invention provides radiolabeled fluoroalkyl tetrabenazine carbinol compounds falling within the scope of generic structure IV comprising a fluorine-18 atom. Fluorine-18 labeled fluoroalkyl tetrabenazine carbinol compounds I and fluoroalkyl tetrabenazine carbinol compounds IV are suitable for use as imaging agents for positron emission tomography (PET) screening of human patients for pathological conditions related to diabetes. Positron emission tomography has become a medical imaging technique of critical importance to human health.

In an alternate embodiment, the present invention provides fluoroalkyl tetrabenazine carbinol compounds falling within the scope of generic structure I and comprising a fluorine-19 atom, a stable isotope of fluorine. The fluoroalkyl tetrabenazine carbinol compounds comprising a fluorine-19 atom are useful in binding studies which allow the identification of those fluoroalkyl tetrabenazine carbinol compounds possessing optimal affinity for a target biomarker, for example VMAT-2. A substantial binding affinity of a given fluorine-19 containing fluoroalkyl tetrabenazine carbinol compound for a target biomarker such as VMAT-2 is a reliable predictor of utility in PET imaging of the corresponding fluorine-18 containing fluoroalkyl tetrabenazine carbinol compound. As is disclosed herein, fluoroalkyl tetrabenazine carbinol compounds I and IV show substantial binding affinity for the biomarker VMAT-2.

Although throughout this disclosure there is considerable focus on human health, the fluoroalkyl tetrabenazine carbinol compounds provided by the present invention are useful in the study and treatment of variety of human and animal diseases as imaging agents, as probes for the development of imaging agents, and as therapeutic agents.

Fluoroalkyl tetrabenazine carbinol compounds having structure I are illustrated in Table 1 below.

TABLE 1

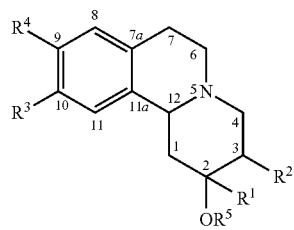

(I)

Examples Of Fluoroalkyl Tetrabenazine Carbinol Compounds Having Structure I

| Entry | $R^1$ | $R^2$ | $R^3$ | $R^4$ | $R^5$ | RP-2 | RP-3 | RP-12 |
|---|---|---|---|---|---|---|---|---|
| 1a | ~~~$^{19}$F | ~~~ | $CH_3$ | $CH_3$ | Ac | R/S | R/S | R/S |
| 1b | ~~~$^{18}$F | ~~~ | $CH_3$ | $CH_3$ | Ac | R | R | R |
| 1c | ≡≡≡$^{19}$F | ~~~ | $CH_3O$ | $CH_3O$ | Ph | R/S | R/S | R/S |
| 1d | ≡≡≡$^{18}$F | ~~~ | $CH_3O$ | $CH_3O$ | H | S | S | S |
| 1e | ~=~$^{19}$F | ~~~ | EtO | $CH_3O$ | Ph | R | S | R |
| 1f | ~=~$^{18}$F | ~~~ | EtO | EtO | Ac | S | R | S |
| 1g | ~O~$^{19}$F | ~~~ | $CH_3CH_2$ | $CH_3$ | Ph | R/S | R/S | R/S |
| 1h | ~O~$^{18}$F | ~~~ | $CH_3O$ | $CH_3O$ | Ac | R | R | R |

TABLE 1-continued

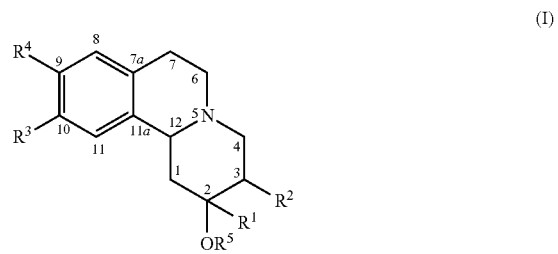

Examples Of Fluoroalkyl Tetrabenazine Carbinol Compounds Having Structure I

| | | | | | | Ring Position* Stereochemistry | | |
|---|---|---|---|---|---|---|---|---|
| Entry | $R^1$ | $R^2$ | $R^3$ | $R^4$ | $R^5$ | RP-2 | RP-3 | RP-12 |
| 1i | (CH(OH)CH$_2^{18}$F) | isobutyl | CH$_3$O | CH$_3$O | H | R/S | R/S | R/S |
| 1j | (CH($^{18}$F)CH$_2^{18}$F) | isobutyl | CH$_3$O | CH$_3$ | Ac | R/S | R/S | R/S |
| 1k | (C(=O)CH$_2^{18}$F) | isobutyl | CH$_3$O | H | H | R | R | R |

*RP-2 = Ring position-2, RP-3 = Ring position-3, RP-12 = Ring position-12

In general, and throughout this disclosure, where no absolute or relative stereochemistry is shown for a structure, as in for example structure I, the structure is intended to encompass all possible absolute and relative stereochemical configurations. Thus, structure I depicts a fluoroalkyl tetrabenazine carbinol compound in which no absolute or relative stereochemistry is shown. As such, structure I is intended to represent a genus of fluoroalkyl tetrabenazine carbinol compounds which includes the racemic compound 1a (Table 1) having both the R configuration and S configuration at ring positions-2, -3 and -12. In another embodiment, structure I represents fluoroalkyl tetrabenazine carbinol compound 1b (Table 1) having the R configuration (absolute stereochemistry) at ring positions-2, -3 and -12. In yet another embodiment, structure I represents compound 1d (Table 1) having absolute stereochemistry opposite that of compound 1b. Those having ordinary skill in the art will appreciate that the individual fluoroalkyl tetrabenazine carbinol compounds shown in Table 1 herein are illustrative of tetrabenazine (TBZ) derivatives falling within the scope of generic structure I.

As noted, in one embodiment, the present invention provides a fluoroalkyl tetrabenazine carbinol compound having structure I which may be a racemic mixture (e.g. compound 1a (Table 1), a single enantiomer (e.g. compound 1b (Table 1), or a composition enantiomerically enriched in a single principal component enantiomer. Entries 2a-2c in Table 2 below illustrate fluoroalkyl tetrabenazine carbinol compounds I comprising a principal component enantiomer and at least one minor component enantiomer.

TABLE 2

Fluoroalkyl Tetrabenazine Carbinol Compounds I Comprising A Principal Component Enantiomer And At Least One Minor Component Enantiomer.

| Entry | Structure of Principal Component Enantiomer | Structure of Minor Component Enantiomer |
|---|---|---|
| 2a | [R,R,R configuration structure] 95 mole % | [S,S,S configuration structure] 5 mole % |

TABLE 2-continued

Fluoroalkyl Tetrabenazine Carbinol Compounds I Comprising A Principal Component Enantiomer And At Least One Minor Component Enantiomer.

| Entry | Structure of Principal Component Enantiomer | Structure of Minor Component Enantiomer |
|---|---|---|
| 2b | 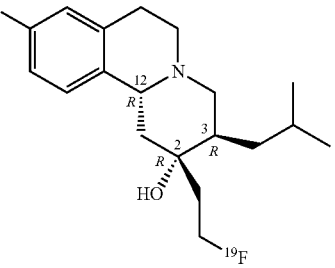<br>98 mole % | 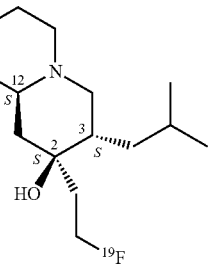 |
| 2c | 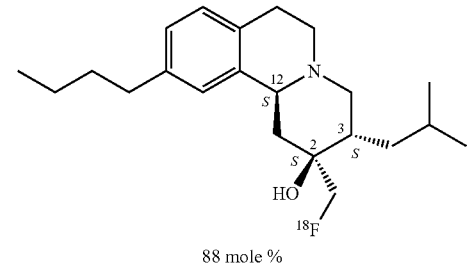<br>88 mole % | 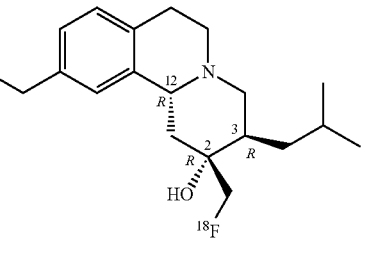 |

In Table 2 the fluoroalkyl tetrabenazine carbinol compositions comprise a principal component enantiomer (the structures appearing under the title heading "Structure of Principal Component Enantiomer") and a "Minor Component Enantiomer". In the fluoroalkyl tetrabenazine carbinol compositions illustrated in Table 2 the mole percentage of the principal component enantiomer is given as "mole %" and refers to the mole percentage of the principal component enantiomer having the structure shown relative to the amounts of all other fluoroalkyl tetrabenazine carbinol components in the composition. For the purposes of this discussion a fluoroalkyl tetrabenazine carbinol is any compound falling within the scope of generic structure I. Entry 2a represents a fluoroalkyl tetrabenazine carbinol composition comprising 95 mole % of the R, R, R principal component enantiomer shown and a lesser amount of the S, S, S minor component enantiomer. Entry 2c represents a fluoroalkyl tetrabenazine carbinol composition comprising 88 mole percent of the S, S, S principal component enantiomer having the structure shown and a lesser amount of the R, R, R minor component enantiomer. Those skilled in the art will appreciate that the fluoroalkyl tetrabenazine carbinol compositions provided by the present invention may comprise a principal component enantiomer, a minor component enantiomer, and additional diastereomeric fluoroalkyl tetrabenazine carbinol components. In one embodiment, the present invention provides a fluoroalkyl tetrabenazine carbinol composition comprising a principal component enantiomer and related diastereomers. In an alternate embodiment, the present invention provides a fluoroalkyl tetrabenazine carbinol composition having no principal component enantiomer and which is a diastereomeric mixture.

In one embodiment, the present invention provides a fluoroalkyl tetrabenazine carbinol compound represented by structure I, which is enantiomerically enriched and is comprised of at least 95 mole percent (mole %) of an enantiomer having the R configuration at ring position-12.

In an alternate embodiment, the present invention provides a fluoroalkyl tetrabenazine carbinol compound represented by structure I, which is enantiomerically enriched and is comprised of at least 95 mole percent (mole %) of an enantiomer having the R configuration at ring position-2.

In one embodiment, the present invention provides a fluoroalkyl tetrabenazine carbinol compound having structure I in which the fluorinated aliphatic radical at ring position-2 (—$R^1$) has a syn-configuration relative to the hydrogen at ring position-12. The principal component enantiomers of Entries 2a-2b of Table 2 illustrate fluoroalkyl tetrabenazine carbinol compounds in which the fluorinated aliphatic moiety at ring position-2 (—$R^1$) has a syn-configuration relative to the hydrogen at ring position-12.

In one embodiment, the present invention provides an enantiomerically enriched fluoroalkyl tetrabenazine carbinol compound comprising a principal component enantiomer having structure II

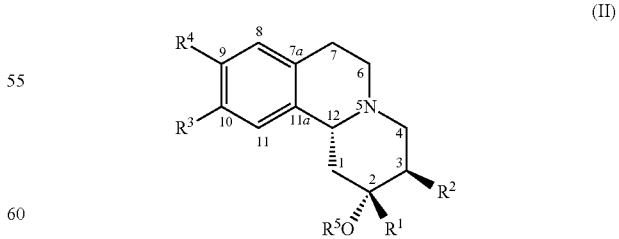

(II)

wherein $R^1$ is a $C_1$-$C_{10}$ fluorinated aliphatic radical; $R^2$ is a $C_1$-$C_{10}$ aliphatic radical; $R^3$ is hydrogen or a $C_1$-$C_{10}$ aliphatic radical; $R^4$ is hydrogen or a $C_1$-$C_{10}$ aliphatic radical; and $R^5$ is hydrogen, a $C_1$-$C_{10}$ aliphatic radical, a $C_2$-$C_{10}$ cycloaliphatic radical, or a $C_2$-$C_{20}$ aromatic radical.

Principal component enantiomers having structure II are illustrated in Table 3 below.

TABLE 3

Principal Component Enantiomers Having Structure II

| Entry | Structure |
|---|---|
| 3a | (R,R,R)-enantiomer: 6,7-dimethoxy/ethoxy tetrabenazine carbinol with isobutyl and fluoroalkyl (19F) substituents |
| 3b | (R,R,R)-enantiomer: ethyl-substituted tetrabenazine carbinol with butyl and 19F-alkyl substituents, OH |
| 3c | (R,R)-enantiomer: 6,7-dimethyl tetrabenazine carbinol with propyl and 18F-alkene substituents, OH |

In one embodiment, the present invention provides an enantiomerically enriched fluoroalkyl tetrabenazine carbinol compound comprising at least 80 mole percent of an enantiomer having structure II, for example the composition comprising the compound of Entry 3a (Table 3) wherein the R, R, R enantiomer shown represents at least 80 mole percent relative to the amounts of all other fluoroalkyl tetrabenazine carbinol components in the composition.

In an alternate embodiment, the present invention provides an enantiomerically enriched fluoroalkyl tetrabenazine carbinol compound which is comprised of at least 95 mole % of an enantiomer having structure II, for example a fluoroalkyl tetrabenazine carbinol composition comprising the compound of Entry 3b (Table 3) wherein the enantiomer shown represents at least 95 mole percent relative to the amounts of all other fluoroalkyl tetrabenazine carbinol components in the composition.

In one embodiment, the present invention provides an enantiomerically enriched fluoroalkyl tetrabenazine carbinol compound comprising a principal component enantiomer having structure III

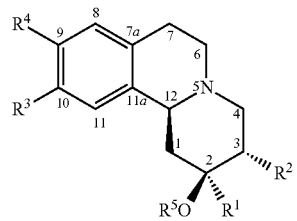

(III)

wherein $R^1$ is a $C_1$-$C_{10}$ fluorinated aliphatic radical; $R^2$ is a $C_1$-$C_{10}$ aliphatic radical; $R^3$ is hydrogen or a $C_1$-$C_{10}$ aliphatic radical; $R^4$ is hydrogen or a $C_1$-$C_{10}$ aliphatic radical; and $R^5$ is hydrogen, a $C_1$-$C_{10}$ aliphatic radical, a $C_2$-$C_{10}$ cycloaliphatic radical, or a $C_2$-$C_{20}$ aromatic radical.

Principal component enantiomers having structure III are illustrated in Table 4 below.

TABLE 4

Principal Component Enantiomers Having Structure III

| Entry | Structure |
|---|---|
| 4a | (S,S,S)-enantiomer: methoxy/silyl-protected tetrabenazine carbinol with fluoroalkyl (19F) substituent, OH |
| 4b | (S,S)-enantiomer: 6,7-dimethyl tetrabenazine carbinol with isobutyl and 18F-alkene substituents, OCH3 |
| 4c | (S,S,S)-enantiomer: 6,7-dimethyl tetrabenazine carbinol with isobutyl and propoxy-ether-18F substituents |

In one embodiment, the present invention provides an enantiomerically enriched fluoroalkyl tetrabenazine carbinol compound comprising at least 80 mole percent of an enantiomer having structure III, for example a fluoroalkyl tetrabenazine carbinol composition comprising the compound of Entry 4a (Table 4) wherein the S, S, S enantiomer shown represents at least 80 mole percent relative to the amounts of all other fluoroalkyl tetrabenazine carbinol components in the composition. In another embodiment, the present invention provides an enantiomerically enriched fluoroalkyl tetrabenazine carbinol compound comprising at least 95 mole percent of an enantiomer having structure III, for example a fluoroalkyl tetrabenazine carbinol composition comprising the compound of Entry 4b (Table 4) wherein the S, S, S enantiomer shown represents at least 95 mole percent relative to the amounts of all other fluoroalkyl tetrabenazine carbinol components in the composition.

As noted, with respect to structures I, II, and III, in one embodiment, the group —OR⁵ is not a hydroxy group and is instead a $C_1$-$C_{10}$ aliphatic radical, a $C_2$-$C_{10}$ cycloaliphatic radical, or a $C_2$-$C_{20}$ aromatic radical. Thus in one embodiment, the group —OR⁵ is an ester moiety, for example an acetate group as exemplified by Entry 1a of Table 1, or for example an aryl ether moiety, for example a phenoxy group as exemplified by Entry 1g of Table 1. In one embodiment, the group —OR⁵ is an aliphatic ester moiety selected from the group consisting of formate, acetate, propanoate, butanoate, pentanoate, hexanoate, and heptanoate. In an alternate embodiment, the group —OR⁵ is a silyl ether moiety, for example triethylsilyloxy.

As noted, the present invention provides novel fluoroalkyl tetrabenazine carbinol compounds I and IV, and in certain embodiments, mixtures thereof. Fluoroalkyl tetrabenazine carbinol compounds having structure IV are illustrated in Table 5 below.

TABLE 5

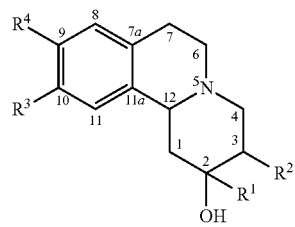

(IV)

Examples Of Fluorophilic Tetrabenazine Carbinol Compound Having Structure IV

| Entry | $R^1$ | $R^2$ | $R^3$ | $R^4$ | Ring Position* Stereochemistry | | |
|---|---|---|---|---|---|---|---|
| | | | | | RP-2 | RP-3 | RP-12 |
| 5a | ~~~¹⁹F | ~~~ | $CH_3$ | $CH_3$ | R/S | R/S | R/S |
| 5b | ~~~¹⁸F | ~~~ | $CH_3$ | $CH_3$ | R | R | R |
| 5c | ~~~¹⁹F | ~~~ | $CH_3O$ | $CH_3O$ | R/S | R/S | R/S |
| 5d | ~~~¹⁸F | ~~~ | $CH_3O$ | $CH_3O$ | S | S | S |
| 5e | ~~~¹⁹F | ~~~ | EtO | $CH_3O$ | R | R | R |
| 5f | ~~~¹⁸F | ~~~ | EtO | EtO | S | R | S |
| 5g | ~~O~~¹⁹F | ~~~ | $CH_3CH_2$ | $CH_3CH_2$ | R/S | R/S | R/S |
| 5h | ~~O~~¹⁸F | ~~~ | $CH_3O$ | $CH_3O$ | R | R | R |
| 5i | ~~OH / ¹⁸F | ~~~ | $CH_3O$ | $CH_3O$ | R/S | R/S | R/S |
| 5j | ¹⁸F / ¹⁸F | ~~~ | $CH_3O$ | $CH_2CH_3$ | R/S | R/S | R/S |

TABLE 5-continued

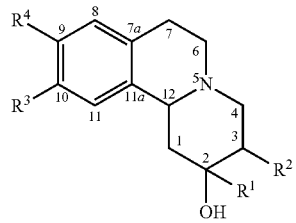

(IV)

Examples Of Fluorophilic Tetrabenazine Carbinol Compound Having Structure IV

| | | | | | Ring Position* Stereochemistry | | |
|---|---|---|---|---|---|---|---|
| Entry | R¹ | R² | R³ | R⁴ | RP-2 | RP-3 | RP-12 |
| 5k | ![](ketone with CH₂-¹⁸F) | isobutyl | CH₃O | H | R | R | R |

Structure IV represents a genus of fluoroalkyl tetrabenazine carbinol compounds which includes the racemic compound 5a (Table 5) having both the R configuration and S configuration at ring positions-2, -3, and -12. In another embodiment, structure IV represents fluoroalkyl tetrabenazine carbinol compound 5b (Table 5) having the R configuration (absolute stereochemistry) at ring positions-2, -3, and -12. In yet another embodiment, structure IV represents compound 5d (Table 5) having absolute stereochemistry opposite that of compound 5b. Those having ordinary skill in the art will appreciate that the individual fluoroalkyl tetrabenazine carbinol compounds shown in Table 5 herein are illustrative of tetrabenazine carbinol derivatives falling within the scope of generic structure IV. Those skilled in the art will appreciate as well that fluoroalkyl tetrabenazine carbinol compounds 5a, 5c, 5g, 5i and 5j represent racemic mixtures.

As noted, in one embodiment, the present invention provides a fluoroalkyl tetrabenazine carbinol compound having structure IV which may be a racemic mixture (e.g. compound 5a (Table 5), a single enantiomer (e.g. compound 5b (Table 5), or a composition enantiomerically enriched in a single principal component enantiomer. Entries 6a-6c in Table 6 below illustrate fluoroalkyl tetrabenazine carbinol compounds IV comprising a principal component enantiomer and at least one minor component enantiomer.

TABLE 6

Fluoroalkyl Tetrabenazine Carbinol Compounds IV Comprising A Principal Component Enantiomer And At Least One Minor Component Enantiomer.

| Entry | Structure of Principal Component Enantiomer | Structure of Minor Component Enantiomer |
|---|---|---|
| 6a | (R,R,R tetrabenazine carbinol with ¹⁸F, H₃CO, H₃CO) 98 mole % | (S,S,S tetrabenazine carbinol with ¹⁸F, H₃CO, H₃CO) |
| 6b | (R,R,R tetrabenazine carbinol with ¹⁹F, EtO) 72 mole % | (S,S,S tetrabenazine carbinol with ¹⁹F, EtO) |

TABLE 6-continued

Fluoroalkyl Tetrabenazine Carbinol Compounds IV Comprising A Principal Component Enantiomer And At Least One Minor Component Enantiomer.

| Entry | Structure of Principal Component Enantiomer | Structure of Minor Component Enantiomer |
|---|---|---|
| 6c | 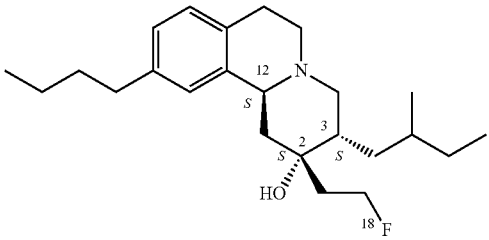 88 mole % | 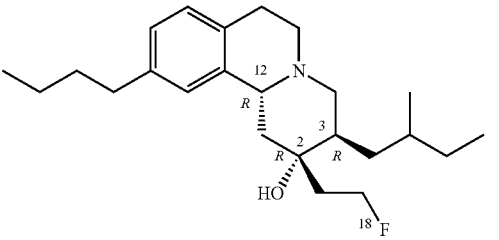 |

In Table 6 the fluoroalkyl tetrabenazine carbinol compositions comprise a principal component enantiomer and a minor component enantiomer. In the fluoroalkyl tetrabenazine carbinol compositions illustrated in Table 6 the mole percentage of the principal component enantiomer is given as "mole %" and refers to the mole percentage of the principal component enantiomer having the structure shown relative to the amounts of all other fluoroalkyl tetrabenazine carbinol components in the composition. For the purposes of this discussion a fluoroalkyl tetrabenazine carbinol is any compound falling within the scope of generic structure I. Those skilled in the art will appreciate that all compounds falling within the scope of generic structure IV also fall within the scope of generic structure I. Entry 6a represents a fluoroalkyl tetrabenazine carbinol composition comprising 98 mole % of the R, R, R principal component enantiomer shown and a lesser amount of the S, S, S minor component enantiomer. Entry 6c represents a fluoroalkyl tetrabenazine carbinol composition comprising 88 mole percent of the S, S, S principal component enantiomer having the structure shown and a lesser amount of the R, R, R minor component enantiomer.

In one embodiment, the present invention provides a fluoroalkyl tetrabenazine carbinol compound represented by structure IV, which is enantiomerically enriched and is comprised of at least 95 mole percent (mole %) of an enantiomer having the R configuration at ring position-12.

In an alternate embodiment, the present invention provides a fluoroalkyl tetrabenazine carbinol compound represented by structure IV, which is enantiomerically enriched and is comprised of at least 95 mole percent (mole %) of an enantiomer having the R configuration at ring position-2.

In one embodiment, the present invention provides a fluoroalkyl tetrabenazine carbinol compound having structure IV in which the fluorinated aliphatic radical at ring position-2 (—$R^1$) has a syn-configuration relative to the hydrogen at ring position-12. The principal component enantiomers of Entries 6a-6c of Table 6 illustrate fluoroalkyl tetrabenazine carbinol compounds in which the fluorinated aliphatic moiety at ring position-2 (—$R^1$) has a syn-configuration relative to the hydrogen at ring position-12.

In one embodiment, the present invention provides an enantiomerically enriched fluoroalkyl tetrabenazine carbinol compound comprising a principal component enantiomer having structure V

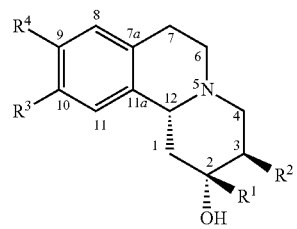

(V)

wherein $R^1$ is a $C_1$-$C_{10}$ fluorinated aliphatic radical; $R^2$ is a $C_1$-$C_{10}$ aliphatic radical; $R^3$ is hydrogen or a $C_1$-$C_{10}$ aliphatic radical; and $R^4$ is hydrogen or a $C_1$-$C_{10}$ aliphatic radical.

Principal component enantiomers having structure V are illustrated in Table 7 below.

TABLE 7

Principal Component Enantiomers Having Structure V

| Entry | Structure |
|---|---|
| 7a | 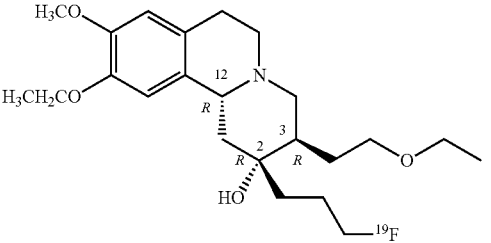 |
| 7b | 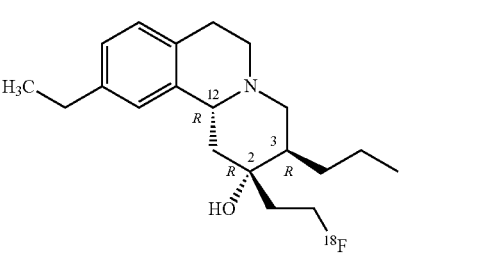 |

TABLE 7-continued

Principal Component Enantiomers Having Structure V

| Entry | Structure |
|---|---|
| 7c | (R,R,R configuration with H₃C, H₃C, HO, and F¹⁸ substituents on tetrabenazine carbinol scaffold) |

In one embodiment, the present invention provides an enantiomerically enriched fluoroalkyl tetrabenazine carbinol compound comprising at least 80 mole percent of an enantiomer having structure V, for example the composition comprising the compound of Entry 7a (Table 7) wherein the R, R, R enantiomer shown represents at least 80 mole percent relative to the amounts of all other fluoroalkyl tetrabenazine carbinol components in the composition.

In an alternate embodiment, the present invention provides an enantiomerically enriched fluoroalkyl tetrabenazine carbinol compound, which is comprised of at least 95 mole % of an enantiomer having structure V, for example an fluoroalkyl tetrabenazine carbinol composition comprising the compound of Entry 7b (Table 7 wherein the R, R, R enantiomer shown represents at least 95 mole percent relative to the amounts of all other fluoroalkyl tetrabenazine carbinol components in the composition.

In one embodiment, the present invention provides an enantiomerically enriched fluoroalkyl tetrabenazine carbinol compound comprising a principal component enantiomer having structure VI

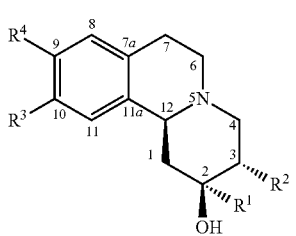

(VI)

wherein R¹ is a $C_1$-$C_{10}$ fluorinated aliphatic radical; R² is a $C_1$-$C_{10}$ aliphatic radical; R³ is hydrogen or a $C_1$-$C_{10}$ aliphatic radical; and R⁴ is hydrogen or a $C_1$-$C_{10}$ aliphatic radical.

Principal component enantiomers having structure VI are illustrated in Table 8 below.

TABLE 8

Principal Component Enantiomers Having Structure VI

| Entry | Structure |
|---|---|
| 8a | (S,S,S configuration; H₃CO, Si(Me)₂t-Bu, HO, ¹⁹F substituents) |
| 8b | (S,S,S configuration; H₃CO, Si(Me)₂t-Bu, HO, ¹⁸F substituents with alkene) |
| 8c | (S,S,S configuration; H₃C, H₃CH₂CO, HO, O–S–¹⁸F substituents) |

In one embodiment, the present invention provides an enantiomerically enriched fluoroalkyl tetrabenazine carbinol compound comprising at least 80 mole percent of an enantiomer having structure VI, for example a fluoroalkyl tetrabenazine carbinol composition comprising the compound of Entry 8a (Table 8) wherein the S, S, S enantiomer shown represents at least 80 mole percent relative to the amounts of all other fluoroalkyl tetrabenazine carbinol components in the composition. In another embodiment, the present invention provides an enantiomerically enriched fluoroalkyl tetrabenazine carbinol compound comprising at least 95 mole percent of an enantiomer having structure VI, for example a fluoroalkyl tetrabenazine carbinol composition comprising the compound of Entry 8b (Table 8) wherein the S, S, S enantiomer shown represents at least 95 mole percent relative to the amounts of all other fluoroalkyl tetrabenazine carbinol components in the composition.

In another embodiment, the present invention provides an enantiomerically enriched fluoroalkyl tetrabenazine carbinol compound having structure IV, wherein R¹ is a $C_1$-$C_{10}$ fluorinated aliphatic radical comprising at least one fluorine-18 atom; R² is a $C_5$-$C_{10}$ aliphatic radical; and R³ and R⁴ are methoxy groups.

As will be clear to one of ordinary skill in the art, the term "fluoroalkyl" refers to the group R¹ of structures I-VI which represents a $C_1$-$C_{10}$ aliphatic radical and is not restricted to the ordinary meaning of the term "alkyl". Thus although the term fluoroalkyl tetrabenazine carbinol is used extensively herein for convenience and means a tetrabenazine compound falling within the scope of generic structure I and comprising a $C_1$-$C_{10}$ fluorinated aliphatic radical at ring position-2.

As noted, the fluoroalkyl tetrabenazine carbinol compounds I, II, III, IV, V, and VI provided by the present invention may comprise a fluorine-18 atom in the fluorinated aliphatic moiety —$R^1$. In various embodiments such fluoroalkyl tetrabenazine carbinol compounds comprising a fluorine-18 atom are useful as PET imaging agents. Thus, in one embodiment, the present invention provides a PET imaging agent comprising a fluoroalkyl tetrabenazine carbinol compound having structure I

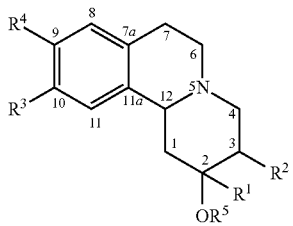
(I)

wherein $R^1$ is a $C_1$-$C_{10}$ fluorinated aliphatic radical comprising at least one fluorine-18 atom; $R^2$ is a $C_1$-$C_{10}$ aliphatic radical; $R^3$ is hydrogen or a $C_1$-$C_{10}$ aliphatic radical; $R^4$ is hydrogen or a $C_1$-$C_{10}$ aliphatic radical; and $R^5$ is hydrogen, a $C_1$-$C_{10}$ aliphatic radical, a $C_2$-$C_{10}$ cycloaliphatic radical, or a $C_2$-$C_{20}$ aromatic radical.

In another embodiment, the present invention provides a PET imaging agent comprising an enantiomerically enriched fluoroalkyl tetrabenazine carbinol compound comprising a principal component enantiomer having structure II

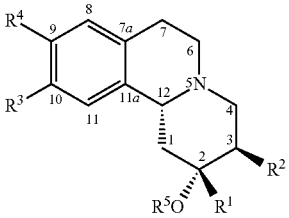
(II)

wherein $R^1$ is a $C_1$-$C_{10}$ fluorinated aliphatic radical comprising at least one fluorine-18 atom; $R^2$ is a $C_1$-$C_{10}$ aliphatic radical; $R^3$ is hydrogen or a $C_1$-$C_{10}$ aliphatic radical; $R^4$ is hydrogen or a $C_1$-$C_{10}$ aliphatic radical; and $R^5$ is hydrogen, a $C_1$-$C_{10}$ aliphatic radical, a $C_2$-$C_{10}$ cycloaliphatic radical, or a $C_2$-$C_{20}$ aromatic radical.

In yet another embodiment, the present invention provides a PET imaging agent comprising an enantiomerically enriched fluoroalkyl tetrabenazine carbinol compound comprising a principal component enantiomer having structure III

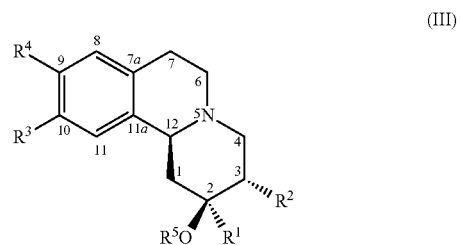
(III)

wherein $R^1$ is a $C_1$-$C_{10}$ fluorinated aliphatic radical comprising at least one fluorine-18 atom; $R^2$ is a $C_1$-$C_{10}$ aliphatic radical; $R^3$ is hydrogen or a $C_1$-$C_{10}$ aliphatic radical; $R^4$ is hydrogen or a $C_1$-$C_{10}$ aliphatic radical; and $R^5$ is hydrogen, a $C_1$-$C_{10}$ aliphatic radical, a $C_2$-$C_{10}$ cycloaliphatic radical, or a $C_2$-$C_{20}$ aromatic radical.

In yet another embodiment, the present invention provides a PET imaging agent comprising a fluoroalkyl tetrabenazine carbinol compound having structure IV

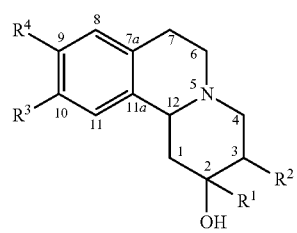
(IV)

wherein $R^1$ is a $C_1$-$C_{10}$ fluorinated aliphatic radical comprising at least one fluorine-18 atom; $R^2$ is a $C_1$-$C_{10}$ aliphatic radical; $R^3$ is hydrogen or a $C_1$-$C_{10}$ aliphatic radical; and $R^4$ is hydrogen or a $C_1$-$C_{10}$ aliphatic radical.

In another embodiment, the present invention provides a PET imaging agent comprising an enantiomerically enriched fluoroalkyl tetrabenazine carbinol compound comprising a principal component enantiomer having structure V

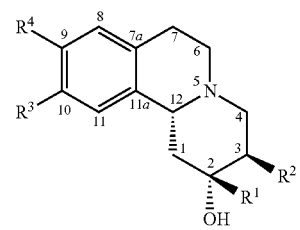
(V)

wherein $R^1$ is a $C_1$-$C_{10}$ fluorinated aliphatic radical comprising at least one fluorine-18 atom; $R^2$ is a $C_1$-$C_{10}$ aliphatic radical; $R^3$ is hydrogen or a $C_1$-$C_{10}$ aliphatic radical; and $R^4$ is hydrogen or a $C_1$-$C_{10}$ aliphatic radical.

In yet another embodiment, the present invention provides a PET imaging agent comprising an enantiomerically enriched fluoroalkyl tetrabenazine carbinol compound comprising a principal component enantiomer having structure VI

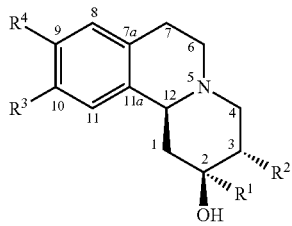

(VI)

wherein $R^1$ is a $C_1$-$C_{10}$ fluorinated aliphatic radical comprising at least one fluorine-18 atom; $R^2$ is a $C_1$-$C_{10}$ aliphatic radical; $R^3$ is hydrogen or a $C_1$-$C_{10}$ aliphatic radical; and $R^4$ is hydrogen or a $C_1$-$C_{10}$ aliphatic radical.

In another embodiment, the present invention provides a PET imaging agent comprising an enantiomerically enriched fluoroalkyl tetrabenazine carbinol compound having structure IV, wherein $R^1$ is a $C_1$-$C_{10}$ fluorinated aliphatic radical comprising at least one fluorine-18 atom; $R^2$ is a $C_5$-$C_{10}$ aliphatic radical; and $R^3$ and $R^4$ are methoxy groups.

The term "PET imaging agent" as used herein refers to a composition comprising a fluorine-18 labeled fluoroalkyl tetrabenazine carbinol compound, which may be administered to a patient in order to perform a PET scan. Typically, the imaging agent is presented to the patient in the form of an aqueous formulation containing a sufficient amount of fluorine-18 labeled fluoroalkyl tetrabenazine carbinol compound to conduct the PET scan. Typically, the amount of fluorine-18 labeled fluoroalkyl tetrabenazine carbinol compound presented to a patient corresponds to a weight of the fluorine-18 labeled fluoroalkyl tetrabenazine carbinol compound on the order of nanograms. In reference to the relative amounts of non-radioactive fluorine-19 containing fluoroalkyl tetrabenazine carbinol compound present in the PET imaging agent presented to a patient, the PET imaging agent typically has a specific activity in a range from about 1 to about 99 percent. In one embodiment, the PET imaging agent has a specific activity in a range from about 10 to about 95 percent. In another embodiment, the PET imaging agent has a specific activity in a range from about 20 to about 90 percent.

The aqueous formulation containing the fluorine-18 fluoroalkyl tetrabenazine carbinol compound is typically administered intravenously and may contain various agents, which promote the dispersal of the PET imaging agent in water. In one embodiment, the PET imagining agent may be administered to a patient in an aqueous formulation comprising ethanol and the fluorine-18 labeled fluoroalkyl tetrabenazine carbinol compound. In an alternate embodiment, the PET imagining agent may be administered to a patient as an aqueous formulation comprising dextrose and the fluorine-18 labeled fluoroalkyl tetrabenazine carbinol compound. In yet another embodiment, the PET imagining agent may be administered to a patient as an aqueous formulation comprising saline and the fluorine-18 labeled fluoroalkyl tetrabenazine carbinol compound.

In addition to being useful as PET imaging agents and as probes for determining the suitability of a given fluoroalkyl tetrabenazine carbinol compound for use as a PET imaging agent, the fluoroalkyl tetrabenazine carbinol compounds provided by the present invention are believed to possess therapeutic utility in the treatment of diseases such as schizophrenia and Huntington's disease. Thus, in one embodiment, the present invention provides a fluoroalkyl tetrabenazine carbinol compound having structure I, which is useful in treating a pathological condition in a patient. In an alternate embodiment, the present invention provides a fluoroalkyl tetrabenazine carbinol compound having structure IV, which is useful in treating a pathological condition in a patient. In various other embodiments, the present invention provides enantiomerically enriched fluoroalkyl tetrabenazine carbinol compounds II, III, V, and VI (and mixtures thereof), which are useful in treating a pathological condition in a patient. Typically the amount of amount of the fluoroalkyl tetrabenazine carbinol compound administered to a patient in a given dose is on the order of milligrams.

Those skilled in the art will appreciate that fluoroalkyl tetrabenazine carbinol compounds falling within the scope of generic structure I may under a variety of conditions form salts which are useful as PET imaging agents, probes for the discovery and development of imaging agents, and/or as therapeutic agents. Thus, the present invention provides a host of novel and useful fluoroalkyl tetrabenazine carbinol compounds and their salts. For example, in one particular embodiment, the present invention provides the hydrochloride salts of the novel fluoroalkyl tetrabenazine carbinol compounds, for example the hydrochloride salt of the compound of Entry 4a of Table 4.

The fluoroalkyl tetrabenazine carbinol compounds of the present invention may be prepared by a variety of methods including those provided in the experimental section of this disclosure. In one embodiment, the fluoroalkyl tetrabenazine carbinol compound is prepared by reaction of nucleophilic fluoride ion or an electrophilic fluorinating agent with a fluorophilic tetrabenazine carbinol compound having structure VII

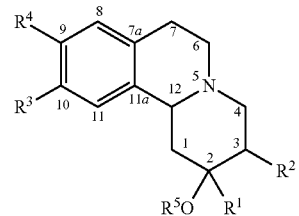

(VII)

wherein $R^1$ is a $C_1$-$C_{20}$ aliphatic, a $C_2$-$C_{20}$ cycloaliphatic radical, or a $C_2$-$C_{20}$ aromatic radical comprising at least one functional group susceptible to reaction with nucleophilic fluoride ion or an electrophilic fluorinating agent; $R^2$ is a $C_1$-$C_{10}$ aliphatic radical; $R^3$ is hydrogen or a $C_1$-$C_{10}$ aliphatic radical; $R^4$ is hydrogen or a $C_1$-$C_{10}$ aliphatic radical; and $R^5$ is hydrogen, a $C_1$-$C_{10}$ aliphatic radical, a $C_2$-$C_{10}$ cycloaliphatic radical, or a $C_2$-$C_{20}$ aromatic radical.

Thus in one embodiment, the present invention provides a fluorophilic tetrabenazine carbinol compound having structure VII. Fluorophilic tetrabenazine carbinol compounds having structure VII are illustrated in Table 9 below.

TABLE 9

Examples Of Fluorophilic Tetrabenazine Compounds Having Structure VII

| Entry | $R^1$ | $R^2$ | $R^3$ | $R^4$ | $R^5$ | Ring Position* Stereochemistry RP-2 | RP-3 | RP-12 |
|---|---|---|---|---|---|---|---|---|
| 9a | 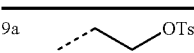 | 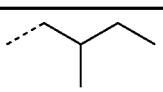 | $CH_3$ | $CH_3$ | Ac | R/S | R/S | R/S |
| 9b | 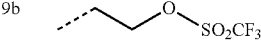 | 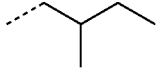 | $CH_3$ | $CH_3$ | Ac | R | R | R |
| 9c | 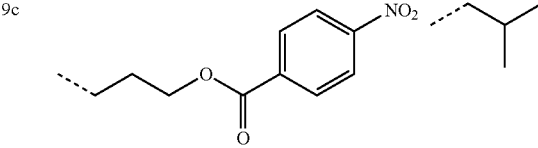 | 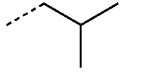 | $CH_3O$ | $CH_3O$ | Ph | R/S | R/S | R/S |
| 9d | 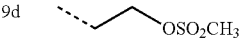 | 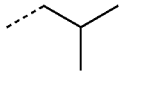 | $CH_3O$ | $CH_3O$ | H | S | S | S |
| 9e | 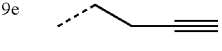 | 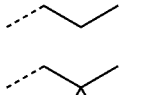 | EtO | $CH_3O$ | Ph | R | S | R |
| 9f | 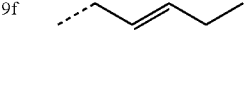 |  | EtO | EtO | Ac | S | R | S |
| 9g |  | 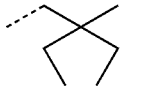 | $CH_3CH_2$ | $CH_3CH_2$ | Ph | R/S | R/S | R/S |
| 9h |  | 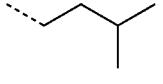 | $CH_3O$ | $CH_3O$ | Ac | R | R | R |
| 9i |  | 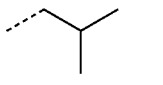 | $CH_3O$ | $CH_2CH_3$ | H | R/S | R/S | R/S |
| 9j | 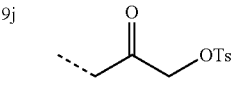 | 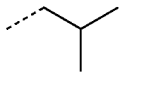 | $CH_3O$ | H | Ac | R/S | R/S | R/S |
| 9k | 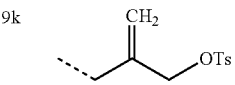 |  | $CH_3O$ | $CH_3O$ | H | R | R | R |
| 9l | 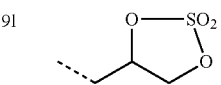 |  | $CH_3O$ | $CH_3O$ | Ph | R | R | R |

As noted, in one embodiment, the present invention provides a fluorophilic compound having structure VII, wherein $R^1$ is a $C_1$-$C_{20}$ aliphatic radical, a $C_2$-$C_{20}$ cycloaliphatic radical, or a $C_2$-$C_{20}$ aromatic radical comprising at least one functional group susceptible to reaction with nucleophilic fluoride ion. In one embodiment, the functional group susceptible to reaction with nucleophilic fluoride ion is an aromatic sulfonate ester (e.g. tosylate, benzenesulfonate, naphthalenesulfonate). In an alternate embodiment, the functional group susceptible to reaction with nucleophilic fluoride ion is an aliphatic sulfonate ester (e.g. methane sulfonate, trifluoromethane sulfonate). In one embodiment, the functional group susceptible to reaction with nucleophilic fluoride ion is selected from the group consisting of tosylate, mesylate, and trifluoromethane sulfonate groups.

In one embodiment, the present invention provides a fluorophilic compound having structure VII wherein the group $R^1$ comprises at least one tosylate group susceptible to reaction with nucleophilic fluoride ion. See for example the Entries 9a, 9j and 9k of Table 9. As defined herein, the tosylate group is an aromatic radical and the group $R^1$ comprising the tosylate group is also an aromatic radical. In the compound shown in Entry 9a for example, the group $R^1$ comprising the tosylate group is a $C_9$ aromatic radical which upon displacement with fluoride ion becomes a $C_2$ fluorinated aliphatic radical.

In an alternate embodiment, the present invention provides a fluorophilic compound having structure VII wherein the group $R^1$ comprises at least one mesylate group susceptible to reaction with nucleophilic fluoride ion. As defined herein, the mesylate group is an aliphatic radical and the group $R^1$ comprising the mesylate group may be an aliphatic, a cycloaliphatic or an aromatic radical depending on the overall structure of the group R'. For example, in a fluorophilic compound having structure VII in which $R^1$ comprises both a mesylate group and an epoxy group, the group $R^1$ is a cycloaliphatic radical. Alternatively, in a fluorophilic compound having structure VII in which $R^1$ comprises both a mesylate group and a tosylate group, the group $R^1$ is an aromatic radical. It is helpful to bear in mind that the definitions of aliphatic, cycloaliphatic and aromatic radicals provided in this disclosure establish a hierarchy in which aliphatic radicals (non-cyclic arrays of atom(s)) must be free of cycloaliphatic groups (a cyclic array of atoms which is not aromatic) and aromatic groups (a cyclic array of atoms which is aromatic), cycloaliphatic radicals must be free of aromatic groups, and aromatic radicals must simply comprise an aromatic group.

In an alternate embodiment, the present invention provides a fluorophilic compound having structure VII wherein the group $R^1$ comprises at least one trifluoromethane sulfonate (triflate) group susceptible to reaction with nucleophilic fluoride ion. See for example Entry 9b of Table 9.

In an alternate embodiment, the present invention provides a fluorophilic compound having structure VII wherein the group $R^1$ comprises at least one p-nitrobenzoate group susceptible to reaction with nucleophilic fluoride ion. See for example Entry 9c of Table 9.

In an alternate embodiment, the present invention provides a fluorophilic compound having structure VII wherein the group $R^1$ comprises at least one methane sulfonate group susceptible to reaction with nucleophilic fluoride ion. See for example Entry 9d of Table 9.

In an alternate embodiment, the present invention provides a fluorophilic compound having structure VII wherein the group $R^1$ comprises at least one epoxy group susceptible to reaction with nucleophilic fluoride ion. See for example Entry 9i of Table 9.

In yet another embodiment, the present invention provides a fluorophilic compound having structure VII wherein the group $R^1$ comprises at least one cyclic sulfate group susceptible to reaction with nucleophilic fluoride ion. See for example Entry 9l of Table 9.

In one embodiment, the present invention provides a fluorophilic compound having structure VII, wherein $R^1$ is a $C_2$-$C_{20}$ aliphatic radical comprising at least one functional group susceptible to reaction with an electrophilic fluorinating agent, for example fluorine gas, perchloryl fluoride, mercuric fluoride, and phenyl selenenyl fluoride.

Thus in one embodiment, the functional group susceptible to reaction with an electrophilic fluorinating agent is selected from the group consisting of carbon-carbon double bonds and carbon-carbon triple bonds. Entries 9e, 9f, 9g, 9h and 9k of Table 9 illustrate compounds falling within the scope of generic structure VII, which are susceptible to reaction with an electrophilic fluorinating agent. Attention is called to Entry 9k wherein the group $R^1$ comprises functional groups susceptible to reaction with an electrophilic fluorinating agent (double bond) and to reaction with nucleophilic fluoride ion (tosylate group).

Fluorophilic tetrabenazine carbinol compounds VII may be prepared in enantiomerically enriched or racemic forms. For example, a fluorophilic tetrabenazine compound VII may be enriched in the R, R, R-enantiomer shown in Entry 9b of Table 9. Alternatively, a fluorophilic tetrabenazine carbinol compound may be enriched in an enantiomer having absolute stereochemistry opposite that of Entry 9b of Table 9, for example the S, S, S-enantiomer of Entry 9d.

Thus, in one embodiment, the present invention provides an enantiomerically enriched fluorophilic tetrabenazine carbinol compound comprising a principal component enantiomer having structure VIII

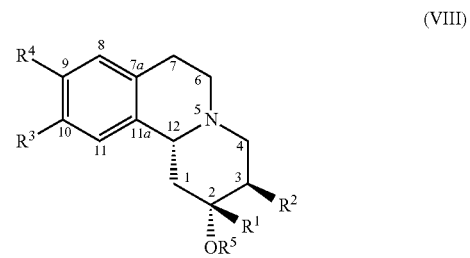

(VIII)

wherein $R^1$ is a $C_1$-$C_{10}$ aliphatic radical, a $C_2$-$C_{20}$ cycloaliphatic radical, or a $C_2$-$C_{20}$ aromatic radical comprising at least one functional group susceptible to reaction with nucleophilic fluoride ion or an electrophilic fluorinating agent; $R^2$ is a $C_1$-$C_{10}$ aliphatic radical; $R^3$ is hydrogen or a $C_1$-$C_{10}$ aliphatic radical; $R^4$ is hydrogen or a $C_1$-$C_{10}$ aliphatic radical; and $R^5$ is hydrogen, a $C_1$-$C_{10}$ aliphatic radical, a $C_2$-$C_{10}$ cycloaliphatic radical, or a $C_2$-$C_{20}$ aromatic radical. Principal component enantiomers VIII are illustrated by Entries 9b, 9h, 9k, and 9l of Table 9.

In an alternate embodiment, the present invention provides an enantiomerically enriched fluorophilic compound comprising a principal component enantiomer having structure IX

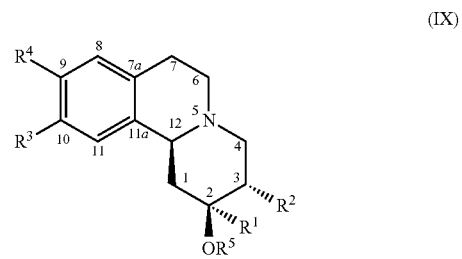

(IX)

wherein $R^1$ is a $C_1$-$C_{10}$ aliphatic radical, a $C_2$-$C_{20}$ cycloaliphatic radical, or a $C_2$-$C_{20}$ aromatic radical comprising at least one functional group susceptible to reaction with nucleophilic fluoride ion or an electrophilic fluorinating agent; $R^2$ is a $C_1$-$C_{10}$ aliphatic radical; $R^3$ is hydrogen or a $C_1$-$C_{10}$ aliphatic radical; $R^4$ is hydrogen or a $C_1$-$C_{10}$ aliphatic radical; and $R^5$ is hydrogen, a $C_1$-$C_{10}$ aliphatic radical, a $C_2$-$C_{10}$ cycloaliphatic radical, or a $C_2$-$C_{20}$ aromatic radical. Principal component enantiomers IX are illustrated by Entry 9d of Table 9.

As noted, with respect to structures VII, VIII, and XI, in one embodiment, the group —OR$^5$ is not a hydroxy group and is instead a $C_1$-$C_{10}$ aliphatic radical, a $C_2$-$C_{10}$ cycloaliphatic radical, or a $C_2$-$C_{20}$ aromatic radical. Thus in one embodiment, the group —OR$^5$ is an ester moiety, for example an acetate group as exemplified by Entry 9a of Table 9, or for example an aryl ether moiety, for example a phenoxy group as exemplified by Entry 9c of Table 9. In one embodiment, the group —OR$^5$ is an aliphatic ester moiety selected from the group consisting of formate, acetate, propanoate, butanoate, pentanoate, hexanoate, and heptanoate. In an alternate embodiment, the group —OR$^5$ is a silyl ether moiety, for example triethylsilyloxy.

Co-pending U.S. patent application Ser. No. 11/760,359 and Ser. No. 11/760,372 filed Jun. 8, 2007 disclose methods for the preparation of racemic and enantiomerically enriched tetrabenazine compositions which may be used for the preparation of fluorophilic tetrabenazine carbinol compounds provided by the present invention. In addition, the Examples Section of the present disclosure provides detailed experimental descriptions of the preparation and characterization of tetrabenazine carbinol compounds VII.

In general, tetrabenazine carbinol compounds VII can be prepared from the corresponding tetrabenazine compound. Tetrabenazine compounds may be prepared by reacting a nucleophilic alkenyl species with an aldehyde compound having structure X

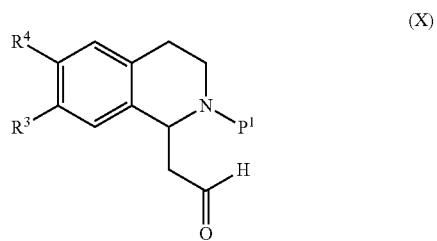

(X)

wherein R$^3$ is hydrogen or a $C_1$-$C_{20}$ aliphatic radical; R$^4$ is hydrogen or a $C_1$-$C_{20}$ aliphatic radical; and R$^3$ is a protecting group, to provide an allylic alcohol (See Method 4 of the Examples section), which is then oxidized to provide an enone designated the "first intermediate" (See Example 1 of the Examples section), the protecting group of which is then removed and the resultant deprotected first intermediate undergoes an amino cyclization reaction to afford the corresponding tetrabenazine (TBZ) compound.

Representative aldehyde compounds encompassed by generic formula X are given in Table 10.

TABLE 10

Representative Aldehyde Compounds Encompassed By Formula X

| Entry | Compound Type | Ring Position* Stereo-chemistry | Structure |
|---|---|---|---|
| 10a | Single "R" enantiomer, "Boc" protecting group P$^1$ | RP-12 "R" | (structure shown) |
| 10b | Single "S" enantiomer, "Boc" protecting group P$^1$ | RP-12 "S" | (structure shown) |
| 10c | Enantiomerically enriched mixture of "R" and "S" enantiomers, "alloc" protecting group P$^1$ | RP-12 "R/S" | (structure shown) 95% |

TABLE 10-continued

Representative Aldehyde Compounds Encompassed By Formula X

| Entry | Compound Type | Ring Position* Stereo- chemistry | Structure |
|---|---|---|---|
| | | | (structure shown, labeled "5%") |
| 10d | Racemic mixture of "R" and "S" enantiomers; "Fmoc" protecting group P[1] | RP-12 "R/S" | (structure) |
| 10e | Racemic mixture of "R" and "S" enantiomers; "Cbz" protecting group P[1] | RP-12 "R/S" | (structure) |
| 10f | Racemic mixture of "R" and "S" enantiomers; "Teoc" protecting group P[1] | RP-12 "R/S" | (structure) |
| 10g | Single "R" enantiomer, "Boc" protecting group P[1] | RP-12 "R" | (structure) |

The preparation of the aldehyde compound featured in Entry 10a of Table 10 is described in the Examples section of this disclosure (Methods 1-3). In general, the class of aldehyde compounds represented by structure X may be prepared by art recognized methods, for example using the methodology depicted in Scheme 1.

Scheme 1

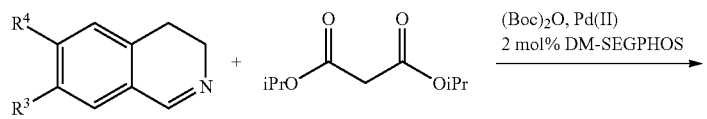

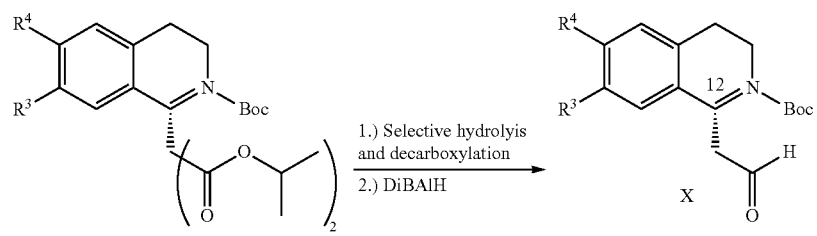

Thus, aldehyde compounds X may be prepared from intermediates prepared using methodology described by Sasamoto et al. (Journal of the American Chemical Society 128, 14010-14011, 2006). Sasamoto et al. disclose the preparation of enantiomerically enriched tetrahydroquinoline malonate compounds, which may be converted to aldehyde compound X by selective hydrolysis of one of the ester moieties of the tetrahydroquinoline malonate and decarboxylation followed by reduction of the resultant tetrahydroisoquinoline monoester to aldehyde compound X as depicted in Scheme 1.

One of ordinary skill in the art will appreciate that the 2 mole percent DM-SEGPHOS shown in Scheme 1 represents a chiral catalyst responsible for the enantiomeric enrichment of the product aldehyde X, and further that the use of DM-SEGPHOS of opposite chirality as the chiral catalyst will afford a product aldehyde X enantiomerically enriched in the "S" enantiomer (aldehyde compound X having the S configuration at ring position-12 (See for example Entry 10b of Table 10). Suitable chiral catalysts include those disclosed by Sasamoto et al. (Journal of the American Chemical Society 128, 14010-14011, 2006), for example (S)-Binap, (R)-Binap, (S)-DM-Binap, (R)-DM-Binap, (S)-DM-SEGPHOS, and (R)-DM-SEGPHOS. Typically use of a catalyst consisting of a ligand possessing a single, for example "S", configuration produces stereochemically enriched malonate adducts of the opposite "R" configuration and vice versa.

In addition to the use of a chiral catalyst to generate aldehyde compounds X enriched in a single configuration at ring position-12, there are available a wide variety of methods for the separation of racemic aldehyde X into its constituent enantiomers. For example, racemic aldehyde compound X may be separated into its constituent enantiomers by high performance liquid chromatography (hplc) on a chiral hplc column.

Other methods for producing enantiomerically enriched compositions provided by the present invention include conversion of a racemic fluoroalkyl tetrabenazine carbinol compound having structure I into an adduct comprising a mixture of diastereomers which are then separated by fractional crystallization. For example, a racemic fluoroalkyl tetrabenazine carbinol compound having structure I may be reacted with (−)-tartaric acid to form an adduct (ammonium tartarate salt) of the racemic fluoroalkyl tetrabenazine carbinol compound, said adduct comprising a mixture of diastereomeric ammonium tartarate salts which are then separated by fractional crystallization.

EXAMPLES

Method 1 Preparation of Protected Diester 2

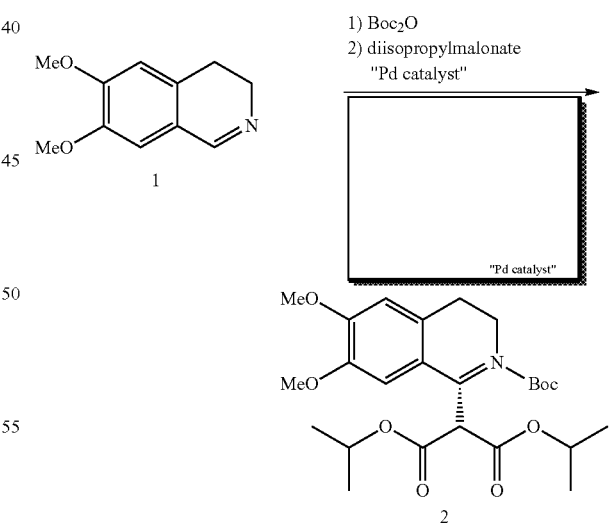

The dihydroisoquinoline 1 (1.0 eq.) and Boc anhydride (1.5 eq.) were dissolved in $CH_2Cl_2$ at room temperature to provide a 1.5 M solution with respect to the dihydroisoquinoline. The mixture was allowed to stir for 30 min. Following the allotted time, the reaction mixture was cooled to 0° C. and then diisopropylmalonate (1.5 eq.) followed by a pre-chilled solution of the Pd catalyst (0.008 eq.) in dichloromethane were added successively to the reaction mixture to provide a final reaction concentration of 0.84 M with respect to the starting dihydroisoquinoline. The reaction mixture was allowed to continue stirring at ~2.5° C. for 15 h. Following this time EtOAc and brine were added to the reaction mixture. The aqueous layer was extracted with three portions of EtOAc and the combined organic layers were dried ($Na_2SO_4$), filtered, and concentrated under reduced pressure to provide the crude product. The crude material was dissolved in a minimal amount of dichloromethane and purified by flash chromatography on $SiO_2$ (15-30% EtOAc-hexanes, elution was observed at 285 nm and 228 nm). The product 2 was a colorless solid that existed as a mixture of rotamers in solution at room temperature 94%: $[\alpha]^{26}_D$ −69.0 (c 0.21, $CHCl_3$); $^1H$ NMR ($CDCl_3$) δ 0.81-1.02 (m, 6H), 1.06-1.17 (m, 6H), 1.23-1.38 (m, 9H), 2.51-2.63 (m, 1H), 2.64-2.77 (m, 1H), 3.20-3.29 (m, 0.6H), 3.32-3.41 (m, 0.4H), 3.51-3.58 (m, 1H), 3.62-3.70 (m, 6H), 3.70-3.76 (m, 0.4H), 3.91-4.01 (m, 0.6H), 4.65-4.82 (m, 1H), 4.83-4.98 (m, 1H), 5.71 (apparent d, J=5.7 Hz, 0.6H), 5.78 (apparent d, J=7.9 Hz, 0.4H), 6.42-6.49 (m, 1H), 6.77 (s, 0.6H), 6.81 (s, 0.4H); $^{13}C$ NMR ($CDCl_3$) δ 21.02, 21.09, 21.18, 21.32, 27.24, 27.95, 28.02, 37.60, 39.34, 52.11, 52.83, 55.48, 55.52, 59.28, 60.08, 68.58, 68.76, 68.82, 79.46, 80.03, 110.09, 110.73, 111.13, 126.11, 126.18, 126.37, 127.07, 146.81, 146.87, 147.93, 153.86, 154.30, 166.29, 166.78, 166.94, 167.06.

Method 2 Selective Hydrolysis and Decarboxylation of Protected Ester 3

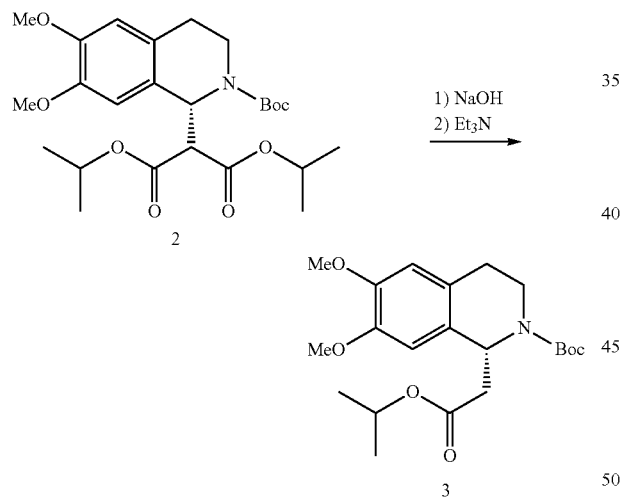

The starting material 2 was taken up in isopropanol to provide a 0.2 M solution of 2. To this solution was added 1M aqueous NaOH, bringing the final concentration of the reaction mixture to 0.1M with respect to the malonate 2. The reaction mixture was heated to and maintained 70° C. for 22 min. (timing was started when the temperature of the reaction mixture temp exceeded 65° C.). Following the allotted time the reaction mixture was quickly cooled to 0° C. The reaction mixture carefully acidified with 2M aqueous HCl and extracted with three portions of dichloromethane. The combined organic extracts dried ($Na_2SO_4$), filtered and concentrated under reduced pressure. The isolated material was taken up in THF to provide a 0.1 M solution (based on the original quantity of 2 used in the reaction mixture) and triethylamine (1.0 eq) was added to the reaction mixture at room temperature. The reaction mixture was heated to its reflux temperature and maintained at this temperature for 90 min. The reaction mixture was concentrated under reduced pressure, dissolved in a minimal quantity of $CH_2Cl_2$ and was immediately purified by column chromatography on $SiO_2$ (15-40% EtOAc-hexanes; 40%, the eluant was monitored at 284 nm). The product 3 existed as a mixture of rotamers at room temperature and was a colorless foam 79%: $[\alpha]^{26}_D$ −82 (c 0.24, $CH_2Cl_2$); $^1H$ NMR ($CDCl_3$) δ 1.19-1.25 (m, 6H), 1.43-1.49 (m, 9H), 2.58-2.69 (m, 2H), 2.70-2.77 (m, 1H), 2.78-2.92 (m, 1H), 3.13-3.43 (m, 1H), 3.81-3.85 (m, 6H), 3.86-4.01 (m, 1H), 4.91-5.05 (m, 1H), 5.38-5.61 (m, 1H), 6.56-6.61 (m, 1H), 6.64-6.70 (s, 1H); $^{13}C$ NMR ($CDCl_3$) δ 21.75, 21.90, 27.93, 28.08, 28.44, 37.53, 38.75, 42.22, 42.81, 51.11, 51.87, 55.92, 56.02, 68.08, 79.74, 80.21, 109.60, 109.99, 111.44, 111.54, 126.28, 126.48, 128.54, 128.76, 147.51, 147.97, 154.39, 154.51, 170.36, 170.59; LRMS-(ESI+) calcd for ($C_{21}H_{31}NO_6$+H) ([M+H]$^+$ 394.22. found 394.16.

Method 3 Preparation of Aldehyde Compound 4

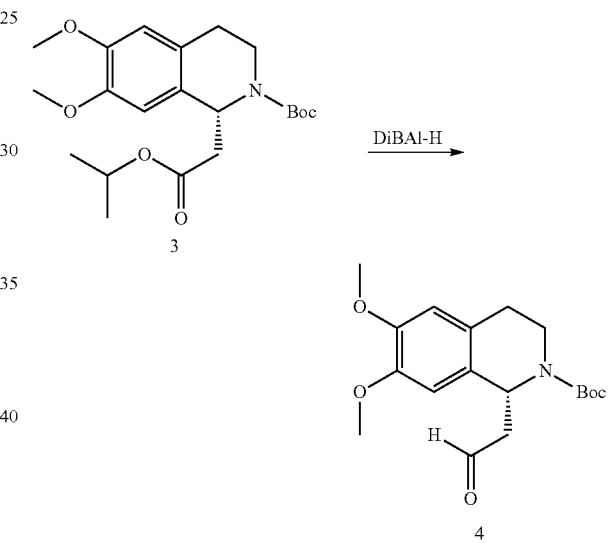

To a 0.12 M solution of the starting monoester (3, 1.0 eq.) in toluene at −78° C. was added a 1.5 M solution of DiBAl—H in hexanes (1.5 eq.) dropwise via a syringe pump. Following the addition the reaction mixture was stirred at −78° C. for 2 h. The reaction mixture was quenched by the addition of EtOAc and was then acidified with saturated aqueous citric acid solution. The reaction mixture was allowed to warm to room temperature and continue stirring for 30 min. The phases were separated, and the aqueous layer extracted with three portions of EtOAc. The combined organic extracts were washed with two portions of 2 M aqueous HCl solution, brine, dried ($MgSO_4$), filtered, and concentrated under reduced pressure. The crude product was subjected purification on $SiO_2$ (15-35% EtOAc-hexanes; Elution was observed at 285 nm and 228 nm). The isolated product, aldehyde compound 4, was a colorless foam. The product existed as a 1:1 mixture of rotamers at room temperature 76%: $[\alpha]^{26}_D$ −116 (c 0.26,$CH_2Cl_2$); $^1H$ NMR ($CDCl_3$) δ 1.40 (s, 9H), 2.58 (apparent t, J=3.8 Hz, 0.5H), 2.61 (apparent t, J=3.5 Hz, 0.5H), 2.68-2.88 (m, 3H), 3.02-3.27 (m, 1H), 3.78 (apparent s, 6H), 3.87-3.99 (m, 0.5H), 4.08-4.23 (m, 0.5H), 5.37-5.68 (m, 1H), 6.55 (s, 1H), 6.58 (s, 1H), 9.78 (s, 1H); $^{13}$C NMR (CDCl$_3$) δ 20.90, 28.02, 28.27, 37.23, 38.65, 49.29, 49.93, 51.12, 55.83, 55.96, 80.13, 80.64, 109.42, 109.52, 111.52, 126.34, 126.51, 127.78, 127.82, 147.72, 147.97, 153.85, 154.62, 200.08, 200.33.

Method 4 Reaction of Aldehyde Compound 4 with Nucleophilic Alkenyl Species Derived from Alkenyl Iodide 5 with to Provide allylic Alcohol 6

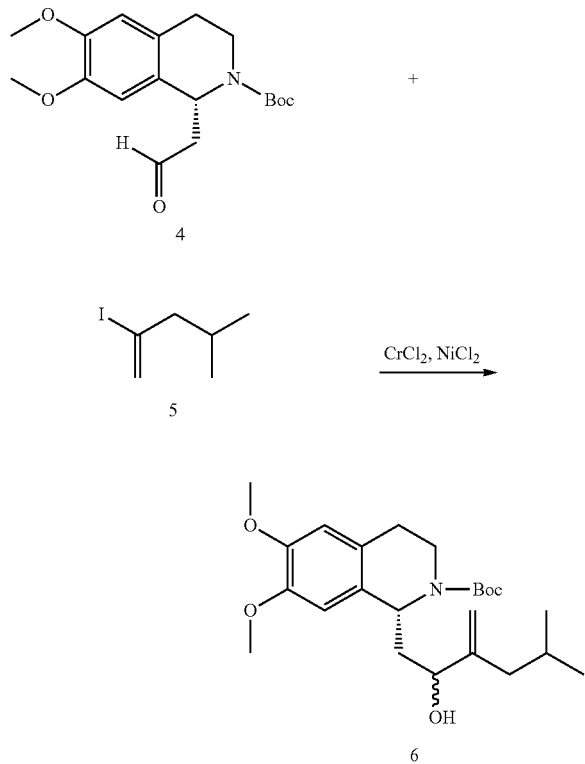

To a neat mixture of the alkenyl iodide 5 (1.0 eq) and the aldehyde compound 4 (1.0 eq.) at room temperature was added 2.65 eq. of chromium chloride doped with 0.5% NiCl$_2$ (w/w). The mixture was vortexed for about 2 min. to provide a homogeneous, green/grey paste and then stirred under nitrogen for an additional 10 min. after which time anhydrous DMF was added to bring the final reaction concentration to 0.36 M. The reaction mixture was deep green in color and was permitted to continue stirring at room temperature for 14 h. Following the allotted time, the reaction mixture was diluted with 1:1 EtOAc-hexanes and an aqueous 0.5 M EDTA solution (pH 9) was added and the entire mixture was allowed to stir for 1.5 h. The aqueous layer was extracted with three portions of EtOAc, dried (MgSO$_4$), filtered, and the filtrate was concentrated under reduced pressure to provide a green oil. The crude material was subjected to column chromatography on SiO$_2$ (35% EtOAc-hexanes; elution was observed at 285 nm and 228 nm). The product allylic alcohol 6 was a pale yellow oil isolated in 53% yield as a mixture of diastereomers, which was taken on to the next step without additional characterization or analysis.

Method 5 Oxidation of allylic Alcohol 6 to Provide First Intermediate 8

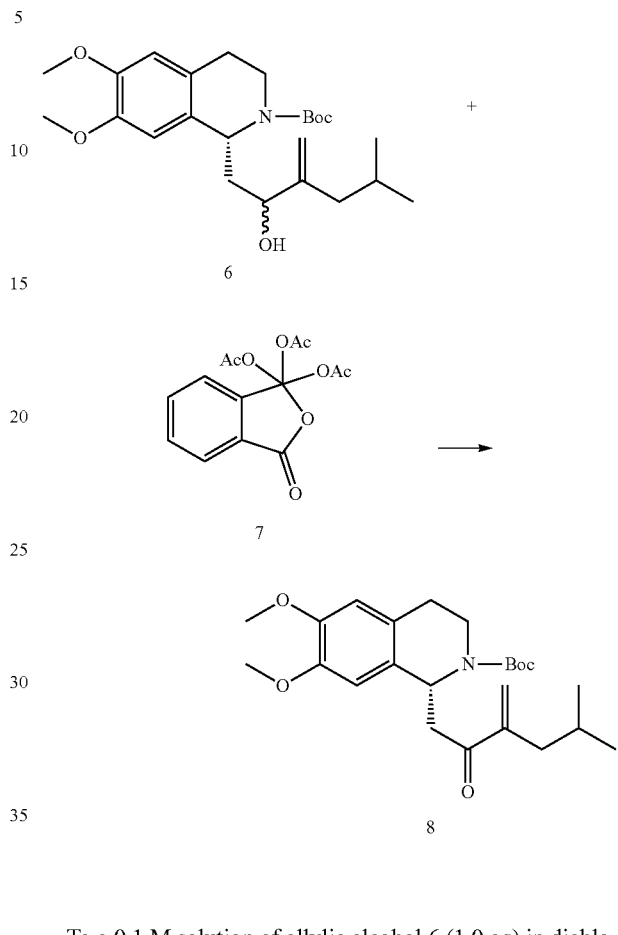

To a 0.1 M solution of allylic alcohol 6 (1.0 eq) in dichloromethane at 0° C. was added 1.1 eq. of the Dess-Martin reagent 7. The reaction mixture was allowed to stir, slowly warming to room temperature over 2.5 h. The reaction was quenched by the addition of saturated aqueous sodium bicarbonate solution and diluted with ethyl acetate. The organic and aqueous layers were partitioned and separated and the aqueous layer extracted with three additional portions of ethyl acetate. The combined organic extracts were washed with brine, dried (MgSO$_4$), filtered, and concentrated under reduced pressure. The crude material was purified by column chromatography on SiO$_2$ (10-30% EtOAc-hexanes, elution was observed at 285 nm and 228 nm). The product first intermediate 8 was a colorless, foul-smelling oil that existed at 26° C. as a 60:40 mixture of rotamers in solution (66%): $^1$H NMR (CDCl$_3$) δ 0.82 (apparent t, J=7.6 Hz, 6H), 1.42 (s, 9H), 1.70 (apparent sept, J=6.62 Hz, 1H), 2.08-2.15 (m, 1H), 2.15-2.24 (m, 1H), 2.62-2.70 (m, 1H), 2.75-2.91 (m, 1H), 2.93-3.07 (m, 1H), 3.07-3.29 (m, 1.6H), 3.30-3.43 (m, 0.4H), 3.79 (s, 3H), 3.81 (s, 3.4H), 4.04-4.16 (m, 0.6H), 5.52-5.62 (m, 1H), 5.69 (s, 1H), 5.90 (s, 0.6H), 6.04 (s, 0.4H), 6.57 (s, 1H), 6.63 (s, 1H); $^{13}$C NMR (CDCl$_3$) δ 22.45, 27.04, 27.25, 28.11, 28.41, 38.01, 39.33, 40.39, 45.20, 45.90, 51.62, 55.92, 55.98, 79.75, 80.23, 109.85, 110.25, 110.28, 111.41, 125.65, 125.72, 126.26, 129.25, 147.57, 147.87, 148.16, 148.29, 148.35, 154.40, 154.51, 199.53; HRMS-(ESI+) calcd for (C$_{24}$H$_{35}$NO$_5$)+H) ([M+H]$^+$ 418.2594. found 418.2590.

Method 5 Removal the Boc Protecting Group First Intermediate 8 and Amino Cyclization Provide (+)-Tetrabenazine 9

Example 1

Conversion of (+)-Tetrabenazine 9 into Tetrabenazine Carbinol Compound 12

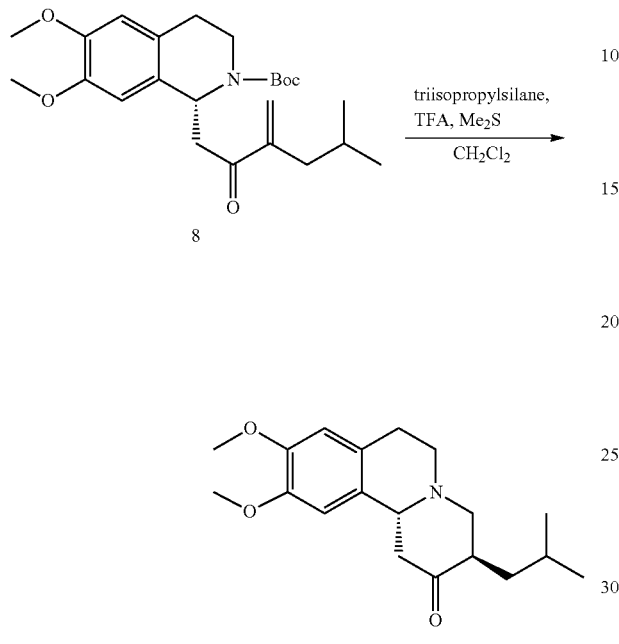

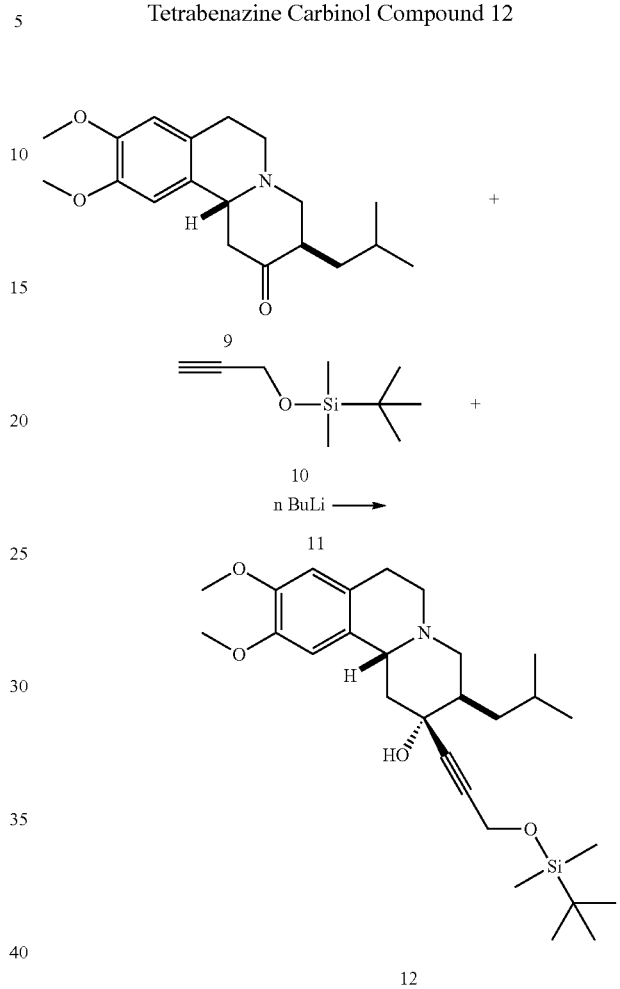

First intermediate 8 (1.0 eq) was dissolved in 10% Me$_2$S-dichloromethane to provide an 82 mM solution. The solution was cooled to 0° C. and triisopropylsilane (1.1 eq.) followed by TFA (precooled to 0° C.) was added to the reaction mixture to provide a final concentration of 41 mM. The reaction mixture was permitted to stir at 0° C. for 1 h. Following the allotted time the reaction mixture was quenched at 0° C. by the addition of saturated aqueous potassium carbonate solution and concentrated under reduced pressure to remove the majority of the dimethylsulfide. The mixture was extracted with five portions of dichloromethane, and the combined organic extracts were washed with brine, dried (MgSO$_4$), filtered and concentrated under reduced pressure to provide the crude product as a yellow solid. The crude product was recrystallized from 3.5% dimethoxyethane in hexanes. The resulting colorless crystals were washed with hexanes to provide pure (+)-tetrabenazine (9) 46%: mp 126.0° C. (3.5% DME-hexanes) (a crystal polymorph was observed at 116° C.); $[\alpha]^{26}_D$ +37.2 (c 0.41, CH$_2$Cl$_2$); $^1$H NMR (CD$_2$Cl$_2$) δ 0.89 (apparent t, J=7.2 Hz, 6H), 0.98 (ddd, J=12, 6.0, 4.0 Hz, 1H), 1.59-1.68 (m, 1H), 1.74 (ddd, J=12, 5.9, 5.7 Hz, 1H), 2.32 (apparent t, J=11.7 Hz, 1H), 2.46 (apparent t, J=12.3 Hz, 1H), 2.55 (ddd, J=12, 10.0, 3.8 Hz, 1H), 2.65-2.73 (m, 2H), 2.83 (dd, J=5.5, 2.8 Hz, 1H), 2.97-3.07 (m, 1H), 3.07-3.14 (m, 1H), 3.25 (dd, J=9.7, 6.3 Hz, 1H), 3.47 (apparent d, J=12 Hz, 1H), 3.75 (s, 3H), 3.77 (s, 3H), 6.55 (s, 1H), 6.60 (s, 1H) $^{13}$C NMR (CD$_2$Cl$_2$) δ 21.98, 23.02, 25.51, 29.46, 35.16, 47.47, 47.63, 50.47, 55.87, 56.01, 61.47, 62.46, 108.46, 111.72, 126.37, 128.96, 147.65, 147.98, 209.72; HRMS-(ESI+) calcd for (C$_{19}$H$_{27}$NO$_3$+H) ([M+H]$^+$ 318.2069. found 318.2082.

To tert-butyldimethyl(prop-2-ynaloxy)silane 10 (0.27 mL, 1.323 mmol) in THF (4 mL) was added nBuLi 11 (0.53 mL, 2.5 M in hexane, 1.323 mmol) dropwise. The mixture was stirred at 0° C. for 0.5 h. To the above reaction mixture tetrabenazine 9 (210 mg, 0.660 mmol) in THF (4 mL) was added dropwise over a period of 10 min. The reaction mixture was stirred at 0° C. for 1 h. Following the allotted time the reaction mixture was quenched by the addition of saturated ammonium chloride (NH$_4$Cl). The mixture was extracted with three portions of EtOAc, and the combined organic extracts were washed with brine, dried over anhydrous Na$_2$SO$_4$, filtered and concentrated provide the crude product. The crude product was chromatographed on SiO$_2$ (12 g, 10% to 60% EtOAc in hexane) to provide 210 mg of the product 12 (diastereomeric mixture, dr=4:1) as a yellow solid (65%). $^1$H NMR (CDCl$_3$) δ 6.64 (s, 1H), 6.54 (s, 1H), 4.40 (s, 2H), 3.84 (s, 6H), 3.46 (d, J=10.0 Hz, 1H), 3.06-3.13 (m, 1H), 2.99-3.02 (m, 1H), 2.95 (dd, J=15.0 & 5.0 Hz, 1H), 2.65 (d, J=15.0 Hz, 1H), 2.49-2.58 (m, 3H), 2.28 (t, J=10.0 Hz, 1H), 1.90-1.96 (m, 1H), 1.77 (t, J=10.0 Hz, 1H), 1.63-1.70 (m, 1H), 1.49-1.54 (m, 1H), 1.21-1.27 (m, 1H), 0.95 (d, J=6.6 Hz, 3H), 0.93 (d, J=6.6 Hz, 3H), 0.91 (s, 9H), 0.14 (s, 6H); $^{13}$C NMR (CDCl$_3$) δ 147.41, 147.10, 129.03, 126.48, 111.47, 107.82, 86.25, 85.11, 72.18, 59.71, 58.54, 55.91, 55.82, 51.76, 51.48, 45.57, 43.92, 37.17, 29.15, 25.80, 25.58, 24.10, 21.84, 18.27.

Example 2

Esterification of Tetrabenazine Carbinol Compound 12 to Provide Acetate 13

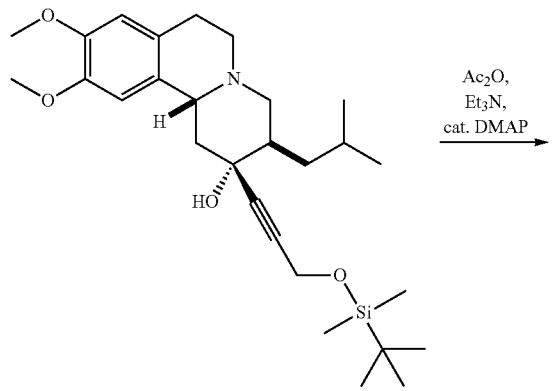
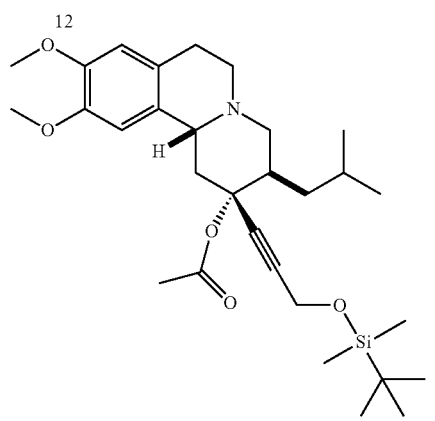

To a solution of (2R,3R,11bR)-2-(3-(tert-Butyldimethylsilyloxy)prop-1-ynyl)-3-isobutyl-9,10-dimethoxy-2,3,4,6,7,11b-hexahydro-1-H-pyrido[2,1-a]isoquinolin-2-ol 12 (140 mg, 0.287 mmol) in $CH_2Cl_2$ (1 mL) (precooled to 0° C.) was added $Ac_2O$ (60 μL, 0.631 mmol), $Et_3N$ (0.12 mL, 0.861 mmol and DMAP (4 mg, 0.03 mmol). The reaction mixture was stirred for 14 h (0° C. to RT). Following the allotted time the reaction mixture was quenched with saturated sodium bicarbonate ($NaHCO_3$). The mixture was extracted with three portions of $CH_2Cl_2$ and the combined organic extracts were washed with brine, dried over anhydrous $Na_2SO_4$, filtered and concentrated to provide the crude product. The crude product was chromatographed on $SiO_2$ (12 g, 10% to 40% EtOAc in hexane) to provide 98 mg of the compound 13 (single diastereomer) as a slightly yellow solid (66%). $^1H$ NMR ($CDCl_3$) δ 6.66 (s, 1H), 6.57 (s, 1H), 4.42 (s, 2H), 3.85 (s, 3H), 3.83 (s, 3H), 3.50 (d, J=11.00 Hz, 1H), 3.39 (dd, J=12.47 & 2.16 Hz, 1H), 3.03-3.10 (m, 1H), 2.96-2.99 (m, 1H), 2.92 (dd, J=12.17 & 4.04 Hz, 1H), 2.65 (d, J=16.05 Hz, 1H), 2.53 (td, J=11.43 & 4.08 Hz, 1H), 2.44 (t, J=11.97 Hz, 1H), 2.12-2.16 (m, 1H), 2.04 (s, 3H), 1.65-1.70 (m, 2H), 1.49-1.55 (m, 1H), 1.20-1.25 (m, 1H), 0.95 (d, J=6.6 Hz, 3H), 0.93 (d, J=6.6 Hz, 3H), 0.91 (s, 9H), 0.14 (s, 6H); $^{13}C$ NMR ($CDCl_3$) δ 169.76, 147.89, 147.61, 129.31, 126.96, 111.88, 108.56, 88.11, 81.61, 79.27, 59.50, 58.31, 56.52, 56.19, 52.16, 51.79, 42.78, 41.59, 37.80, 29.61, 26.15, 26.09, 24.28, 22.44, 18.59, 4.61, 4.71.

Example 3

Deprotection of Acetate 13 to Tetrabenazine Carbinol Compound 14

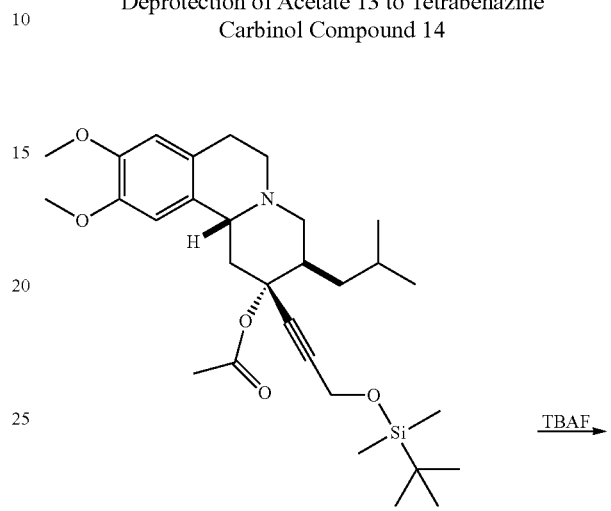
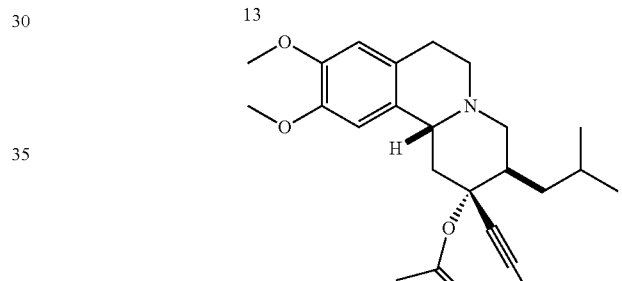

A solution of (2R,3R,11bR)-2-(3-(tert-Butyldimethylsilyloxy)prop-1-ynyl)-3-isobutyl-9,10-dimethoxy-2,3,4,6,7,11b-hexahydro-1-H-pyrido[2,1-a]isoquinolin-2-yl acetate 13 (98 mg, 0.185 mmol) in THF (1 mL) was added dropwise a solution of TBAF (0.56 mL, 1M in THF, 0.555 mmol) at 0° C. The reaction mixture was stirred (0° C. to RT) for 2 h. After the allotted time the reaction mixture was quenched with saturated ammonium chloride ($NH_4Cl$). The mixture was extracted with three portions of EtOAc and the combined organic extracts were washed with brine, dried over anhydrous $Na_2SO_4$, filtered and concentrated to provide the crude product. The crude product was chromatographed on $SiO_2$ (12 g, 10% to 50% EtOAc in hexane) to produce 68 mg of the compound 14 as a slightly yellow solid (88%). $^1H$ NMR ($CDCl_3$) δ 6.67 (s, 1H), 6.57 (s, 1H), 4.35 (s, 2H), 3.86 (s, 3H), 3.83 (s, 3H), 3.49 (d, J=12.00 Hz, 1H), 3.35 (d, J=11.24 Hz, 1H), 3.04-3.10 (m, 1H), 2.97-3.00 (m, 1H), 2.92 (dd, J=12.04 & 3.68 Hz, 1H), 2.75 (br s, 1H), 2.65 (d, J=14.99 Hz, 1H), 2.49-2.54 (m, 1H), 2.39-2.44 (m, 1H), 2.10-2.16 (m, 1H), 2.05 (s, 3H), 1.63-1.70 (m, 2H), 1.50 (td, J=13.58 & 2.95 Hz, 1H), 1.16-1.21 (m, 1H), 0.95 (d, J=6.60 Hz, 3H), 0.93 (d, J=6.60 Hz, 3H); $^{13}C$ NMR ($CDCl_3$) δ 170.20, 147.99, 147.64, 129.03, 126.86, 111.92, 108.65, 88.42, 82.15, 79.31, 59.40, 58.22, 56.58, 56.20, 51.62, 51.31, 42.59, 41.49, 37.62, 29.49, 26.11, 26.05, 24.49, 22.42.

Example 4

Preparation of Fluorophilic Tetrabenazine Carbinol Compound, Mesylate 15

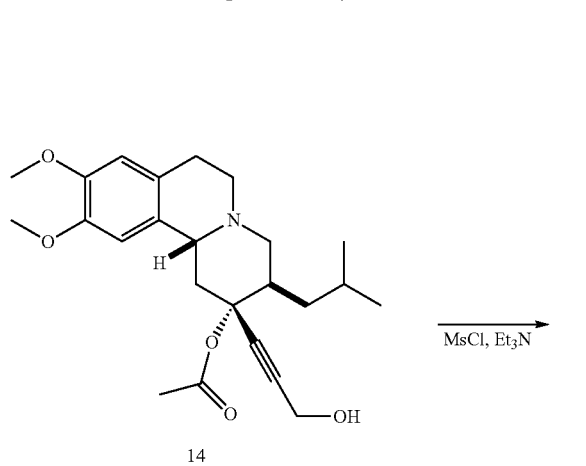

To a 0° C. solution of (2R,3R,11bR)-2-(3-hydroxyprop-1-ynyl)-3-isobutyl-9,10-dimethoxy-2,3,4,6,7,11b-hexahydro-1-H-pyrido[2,1-a]isoquinolin-2-yl acetate 14 (60 mg, 0.144 mmol) in $CH_2Cl_2$ (1.5 mL) was added dropwise $Et_3N$ (61 µL, 0.433 mmol) followed by methanesulfonyl chloride (MsCl) (17 µl, 0.216 mmol). The reaction mixture was stirred at 0° C. for about 2 h. After the allotted time the reaction mixture was poured into cold water and layers separated. The reaction mixture was extracted with three portions of $CH_2Cl_2$ and the combined organic extracts were dried over anhydrous $Na_2SO_4$, filtered and concentrated. The residue was chromatographed on $SiO_2$ (12 g, 10% to 70% EtOAc in hexane) to give 38 mg of the product as a yellow solid of compound 15 (53%).

Example 5

Preparation of Fluoroalkyl Tetrabenazine Carbinol Compound 16

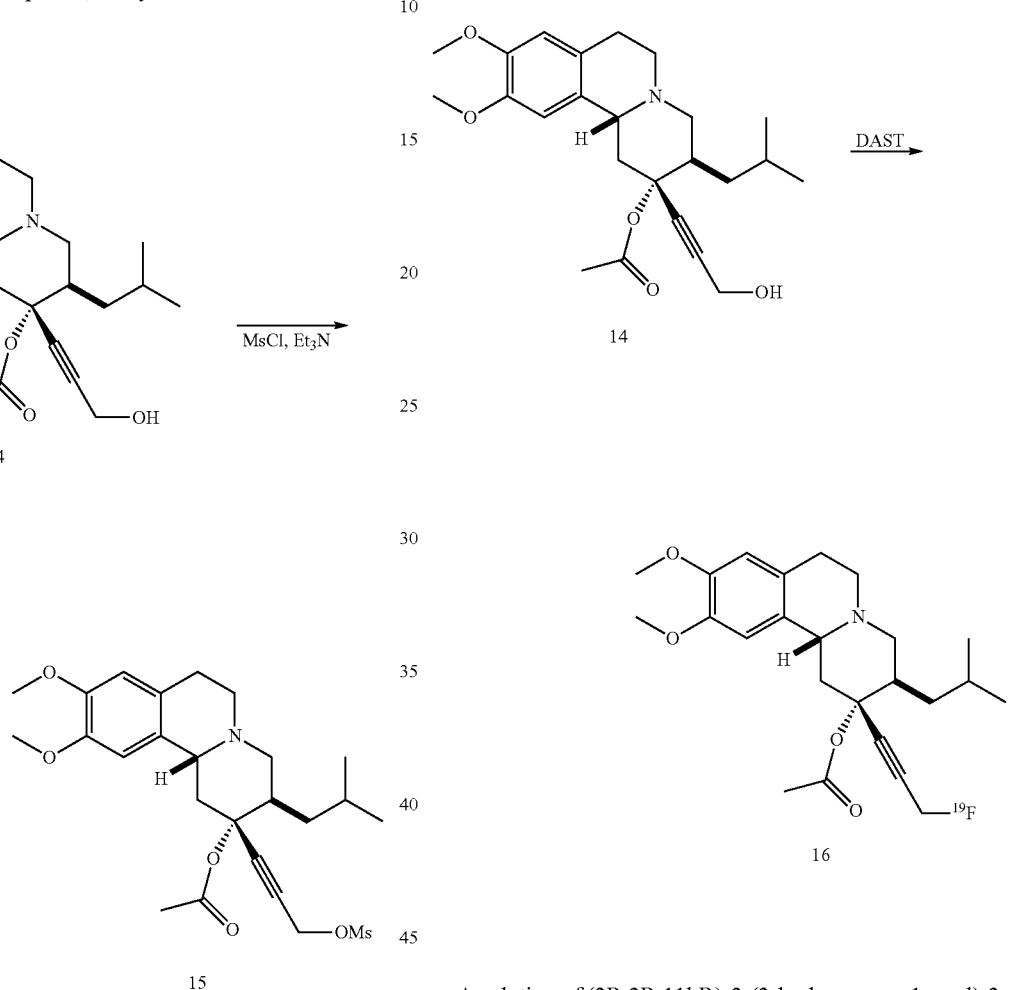

A solution of (2R,3R,11bR)-2-(3-hydroxyprop-1-ynyl)-3-isobutyl-9,10-dimethoxy-2,3,4,6,7,11b-hexahydro-1-H-pyrido[2,1-a]isoquinolin-2-yl acetate 14 (10 mg, 0.024 mmol) in $CH_2Cl_2$ (0.5 mL) was cooled to −78° C. To this cooled solution was added dropwise a solution of (diethylamino)sulfur trifluoride (DAST) (10 µL, 0.072 mmol) in $CH_2Cl_2$ (0.1 mL). The reaction mixture was stirred (−78° C. to RT) for 4 h. The reaction mixture was then quenched with water and extracted with three portions of $CH_2Cl_2$. The combined organic extracts were dried over anhydrous $Na_2SO_4$, filtered and concentrated. The residue was chromatographed on $SiO_2$ (0% to 10% MeOH in $CH_2Cl_2$) to give 3 mg of the product 16 as a white solid (30%). $^1$H NMR ($CDCl_3$) δ 6.68 (s, 1H), 6.60 (s, 1H), 5.10 (d, J=47.43 Hz, 2H), 3.88 (s, 3H), 3.86 (s, 3H), 3.49 (d, J=11.56 Hz, 1H), 3.40 (dd, J=12.40 & 2.36 Hz, 1H), 3.06-3.12 (m, 1H), 2.95-3.02 (m, 2H), 2.68 (d, J=15.12 Hz, 1H), 2.57 (td, J=11.03 & 4.09 Hz, 1H), 2.44 (d, J=11.85 Hz, 1H), 2.10-2.21 (m, 1H), 2.09 (s, 3H), 1.70 (t, J=11.04, 2H), 1.51-1.56 (m, 1H), 1.20-1.25 (m, 1H), 0.99 (d, J=6.62 Hz, 3H), 0.95 (d, J=6.62 Hz, 3H).

Example 6

Preparation of Fluoroalkyl Tetrabenazine Carbinol Compound 17

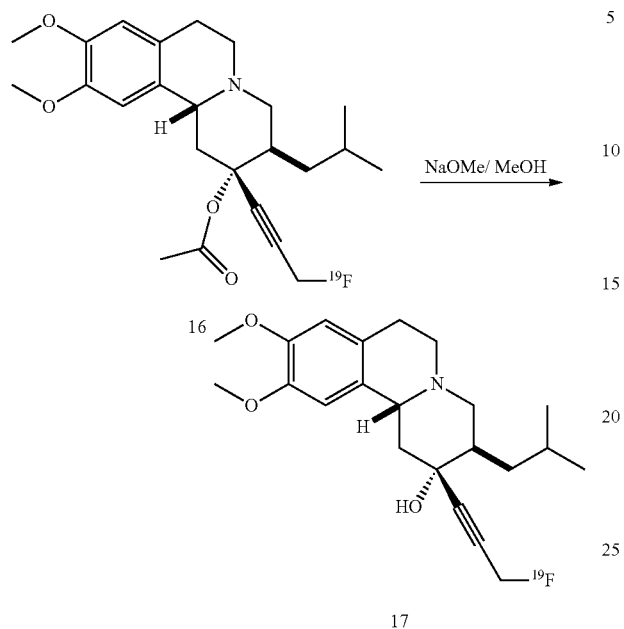

The starting fluoroalkyl tetrabenazine carbinol compound (2R,3R,11bR)-2-(3-fluoroprop-1-ynyl)-3-isobutyl-9,10-dimethoxy-2,3,4,6,7,11b-hexahydro-1-H-pyrido[2,1-a]isoquinolin-2-yl acetate 16 (1.8 mg, 0.0043 mmol) was added to 1 mL of a solution prepared by dissolution of freshly cut sodium (1 mg, 0.043 mmol) in cold MeOH (10 mL). The mixture was stirred at room temperature for 2 h. The mixture was concentrated under a stream of $N_2$ and dissolved in saturated ammonium chloride ($NH_4Cl$). Following the allotted time the mixture was extracted with three portions of $CH_2Cl_2$ and the combined organic extracts were dried over anhydrous $Na_2SO_4$, filtered, concentrated and dried under vacuum to give 1.5 mg of the product as a white solid 17 which was >95% pure by HPLC analysis (92%). HRMS calcd. for (M+H) 376.2288. found 376.2290.

Example 7

Preparation of Tetrabenazine Carbinol Compound, Diol 18

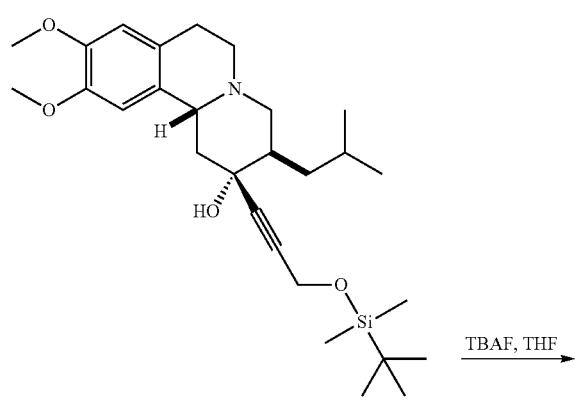

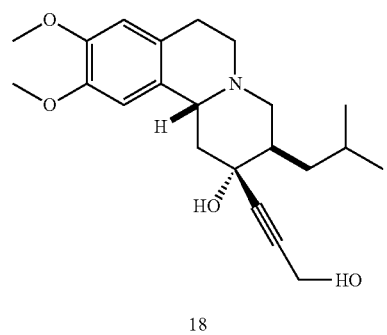

To a precooled (0° C.) solution of tetrabenazine carbinol compound, 12 (112 mg, 0.220 mmol) in 2 mL of THF, was added dropwise a solution of TBAF (330 ml, 0.33 mmol, 1M in THF). The mixture is stirred at room temperature for 12 h. Following the allotted time the reaction mixture was quenched by the addition of saturated ammonium chloride ($NH_4Cl$). The mixture was extracted with three portions of EtOAc, and the combined organic extracts were washed with brine, dried over anhydrous $Na_2SO_4$, filtered and concentrated to provide a product. The product was chromatographed on $SiO_2$ (12 g, 0% to 10% MeOH in $CH_2Cl_2$) to produce 49 mg of the tetrabenazine carbinol compound, diol 18 as a slightly yellow solid (60%). $^1$H NMR (CDCl$_3$) δ 6.67 (s, 1H), 6.57 (s, 1H), 3.42 (d, J=11.3 Hz, 1H), 3.14-3.21 (m, 1H), 2.94-3.00 (m, 2H), 2.62 (t, J=10.2 Hz, 2H), 2.50 (td, J=11.2 & 4.0 Hz, 1H), 2.17-2.26 (m, 2H), 2.08 (t, J=9.6 Hz, 1H), 1.61-1.72 (m, 2H), 1.21-1.29 (m, 1H), 1.02 (d, J=6.6 Hz, 3H, 0.99 (d, J=6.6 Hz, 3H); $^{13}$C NMR (CDCl$_3$) δ 148.1, 147.59, 128.67, 123.63, 111.85, 108.43, 88.70, 84.75, 72, 31, 60.64, 58.64, 56.55, 56.05, 52.36, 50.36, 44.19, 37.01, 28.73, 25.89, 24.64, 22.50.

Example 8

Preparation of Fluorophilic Tetrabenazine Carbinol Compound, Mesylate 19

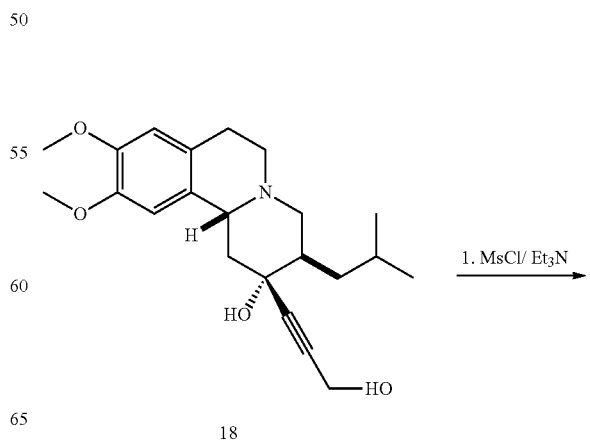

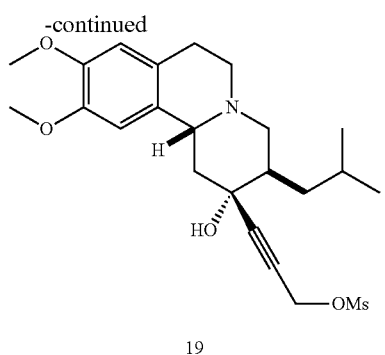

19

To a 0° C. solution of diol 18 (1 equivalent) in CH$_2$Cl$_2$ is added dropwise Et$_3$N (3 equivalents) followed by methanesulfonyl chloride (MsCl) (1.5 equivalents). The reaction mixture is stirred at 0° C. for about 2 h. After the allotted time the reaction mixture is poured into cold water and layers are separated. The quenched reaction mixture is extracted with three portions of CH$_2$Cl$_2$ and the combined organic extracts are dried over anhydrous Na$_2$SO$_4$, filtered and concentrated. The residue may be chromatographed on SiO$_2$ (10% to 70% EtOAc in hexane) to provide the product mesylate 19.

Example 9

Preparation of PET Imaging Agent 20

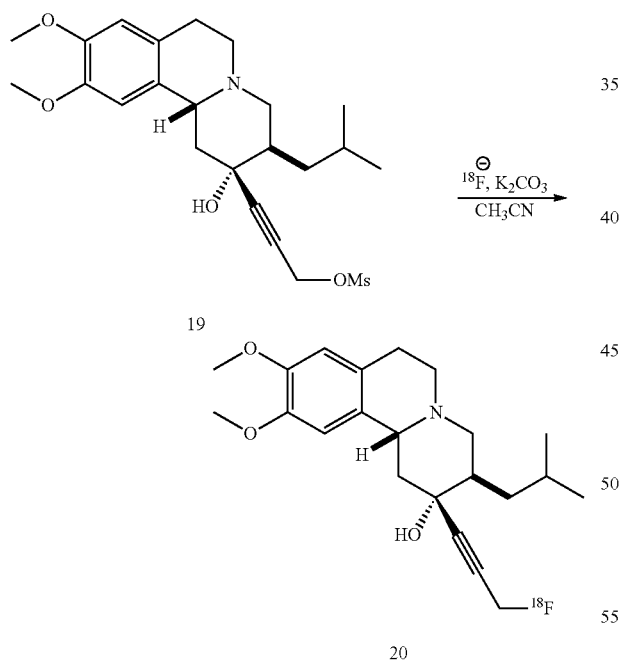

To a Teflon-lined reaction vial contained in a shielded hood and fitted with a nitrogen purge inlet and magnetic spin bar, is added about 1 milliliter of an aqueous acetonitrile solution F-18 fluoride ion, potassium carbonate (about 1 mg), and Kryptofix 221 (about 10 mg). The vial is heated at 100° C. under a stream of nitrogen to effect the azeotropic removal of water. Additional dry acetonitrile (1 mL) is added and evaporated. This azeotropic drying protocol is repeated three times. After the final evaporation step a mixture of dimethyl formamide and acetonitrile (about 1 mL) containing the fluorophilic tetrabenazine carbinol compound, mesylate 20, (2 mg) is added and the vial is sealed. The reaction mixture is stirred and heated at 100° C. for 10 minutes and then is cooled to room temperature. The product mixture comprising the starting mesylate 19 and the product F-18 labeled fluoroalkyl tetrabenazine carbinol compound 20 is diluted with water (10 mL) and applied to a Sep-Pak cartridge. The cartridge is then washed with water (3×) to remove unreacted fluoride ion and other water soluble components of the product mixture. The radiolabled fluoroalkyl tetrabenazine carbinol compound 20 and starting mesylate 19 are then eluted from the cartridge with acetonitrile. Most of the acetonitrile is then evaporated and the residue is dissolved in aqueous acetonitrile and subjected to preparative reverse phase HPLC to afford an aqueous formulation comprising PET imaging agent 20.

Method 6 Reduction of (+)-Tetrabenazine 9 to a Diasteromeric Mixture of Dihydrotetrabenazine Compounds 21 and 22

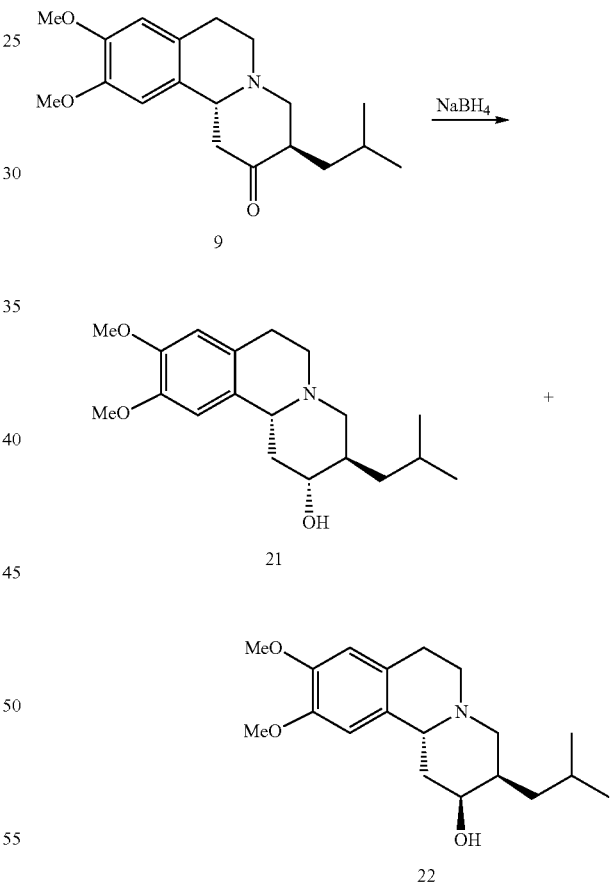

To a 0.11 M solution of (+)-TBZ (9) in ethanol at 0° C. was added NaBH$_4$ (2.85 eq). The reaction mixture was allowed to stir for 60 min. at room temperature. The solvent was carefully removed under reduced pressure, and the residue was taken up in dichloromethane and washed with three portions of saturated aqueous K$_2$CO$_3$. The aqueous washings were back extracted with two portions of dichloromethane. The combined organic extracts were dried (MgSO$_4$), filtered, and concentrated under reduced pressure to provide a colorless oil that crystallized on standing under high vacuum. Purification of the crude product was achieved by chromatography on SiO$_2$ (2.5-5% MeOH—CH$_2$Cl$_2$, elution was observed at 285 nm) UV active fractions were reanalyzed by TLC. Two products, 21 and 22, were isolated from this procedure. The major product 21 was a colorless solid 74%: [α]$^{26}_D$ +48 (c 0.30, CH$_2$Cl$_2$) $^1$H NMR (CD$_2$Cl$_2$) δ 0.93 (d, J=6.6 Hz, 3H), 0.95 (d, J=6.6 Hz, 3H), 1.04 (ddd, J=14.6, 8.7, 4.3 Hz, 1H), 1.42 (dd, J=20.2, 11.4 Hz, 1H), 1.59 (ddd, J=13.7, 9.6, 3.3 Hz, 1H), 1.64-1.78 (m, 2H), 1.96 (apparent t, J=11.4 Hz, 1H), 2.27 (br s, 1H), 2.40-2.48 (m, 1H), 2.54 (ddd, J=12.3, 3.7, 2.3 Hz, 1H), 2.60-2.67 (m, 1H), 2.95-3.09 (m, 3H), 3.11 (apparent d, J=11.1 Hz, 1H), 3.35 (ddd, J=10.4, 10.4, 4.5 Hz, 1H), 3.80-3.81 (m, 6H), 6.60 (s, 1H), 6.69 (s, 1H); $^{13}$C NMR (CD$_2$Cl$_2$) δ 21.61, 24.02, 25.33, 29.30, 39.68, 40.81, 41.58, 51.83, 55.74, 55.91, 60.02, 60.92, 74.32, 108.42, 111.73, 126.68, 129.76, 147.35, 147.61; HRMS-(ESI+) calcd for (C$_{19}$H$_{29}$NO$_3$+H) [M+H]$^+$ 320.2226. found 320.2242. The minor product 22 was a yellow oil 4%: $^1$H NMR (CD$_2$Cl$_2$) δ 0.94 (d, J=6.6 Hz, 3H), 0.96 (d, J=6.6 Hz, 3H), 1.13-1.20 (m, 1H), 1.24-1.34 (m, 2H), 1.60-1.77 (m, 2H), 1.89-2.00 (m, 1H) 2.36-2.44 (m, 2H), 2.53 (ddd, J=10.5, 10.5, 3.8 Hz, 1H), 2.58-2.70 (m, 2H), 2.91-2.98 (m, 1H), 2.98-3.09 (m, 1H), 3.48 (apparent d, J=11.6 Hz, 1H), 3.80-3.82 (apparent s, 6H), 4.07 (apparent d, J=3.1 Hz, 1H), 6.60 (s, 1H), 6.68 (s, 1H); $^{13}$C NMR (CD$_2$Cl$_2$) δ 22.74, 22.81, 24.87, 29.30, 37.83, 38.87, 39.42, 52.44, 55.76, 55.96, 56.32, 56.43, 67.88, 108.45, 111.78, 127.18, 130.38, 147.30, 147.54.

Measurement of Binding Affinity of Fluoroalkyl Tetrabenazine Carbinol Compounds to VMAT-2

VMAT-2 binding affinities were measured for fluoroalkyl tetrabenazine carbinol compounds 16 and 17 provided by the present invention. VMAT-2 binding affinity measurements were carried out by Novascreen Biosciences Corporation (Hanover, Md., USA) using protocol Cat. No. 100-0751. Novascreen, Inc. is a commercial provider of biological assays for the pharmaceutical industry. Binding affinity data are presented in Table 11 and illustrate very high binding affinity for the fluoroalkyl tetrabenazine carbinol compounds of the present invention (compounds 16 and 17) relative to a reserpine control (Comparative Example 1) and a dihydrotetrabenazine (DTBZ) control (Comparative Example 2). The data obtained for fluoroalkyl tetrabenazine carbinol compounds 16 and 17 reveal an unexpected tolerance of fluoroalkyl substitution at ring position-2, which combines a change in the size and lipophilicity of the group at ring position-2 with the uncertainty which arises whenever a hydrogen in a biologically active molecule is replaced by fluorine. In addition, the binding constants Ki expressed in nano-molar (nM) concentration units indicate a very high affinity of the fluoroalkyl tetrabenazine carbinol compounds of the present invention for the VMAT-2 biomarker.

TABLE 11

VMAT-2 Binding Affinity of Fluoroalkyl Tetrabenazine Carbinol Compounds 16 and 17

| Example No. | Compound No. | Structure | Ki (nM) |
|---|---|---|---|
| Example 5 | 16 | 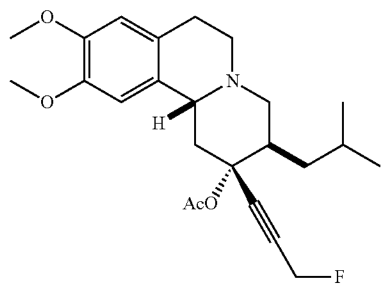 | 19 |
| Example 6 | 17 | 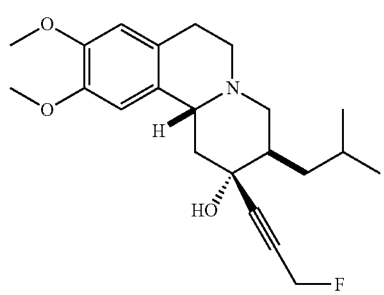 | 19 |

TABLE 11-continued

VMAT-2 Binding Affinity of Fluoroalkyl Tetrabenazine Carbinol Compounds 16 and 17

| Example No. | Compound No. | Structure | Ki (nM) |
|---|---|---|---|
| Comparative Example 1 | Reserpine 23 | 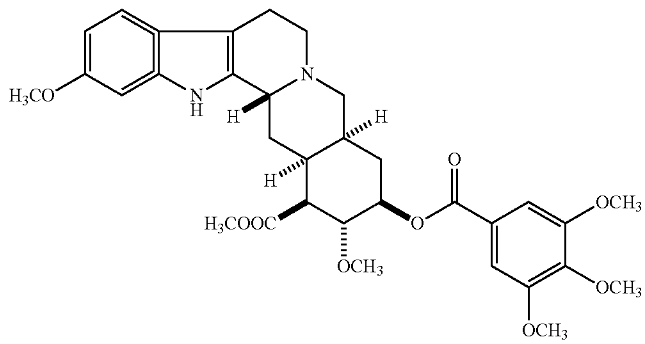 | 162* |
| Comparative Example 2 | DTBZ 21 | (+)-DTBZ | 3 |

*Average of two Ki values obtained for reserpine 70 nM and 254 nM

The foregoing examples are merely illustrative, serving to illustrate only some of the features of the invention. The appended claims are intended to claim the invention as broadly as it has been conceived and the examples herein presented are illustrative of selected embodiments from a manifold of all possible embodiments. Accordingly, it is the Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of" Where necessary, ranges have been supplied; those ranges are inclusive of all sub-ranges there between. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims.

What is claimed is:

1. A fluoroalkyl tetrabenazine compound having structure I (I)

wherein $R^1$ is a $C_1$-$C_{10}$ fluorinated aliphatic radical; $R^2$ is a $C_1$-$C_{10}$ aliphatic radical; $R^3$ is hydrogen or a $C_1$-$C_{10}$ aliphatic radical; $R^4$ is hydrogen or a $C_1$-$C_{10}$ aliphatic radical; and $R^5$ is hydrogen, a $C_1$-$C_{10}$ aliphatic radical, a $C_2$-$C_{10}$ cycloaliphatic radical, or a $C_2$-$C_{20}$ aromatic radical.

2. The fluoroalkyl tetrabenazine compound according to claim 1, comprising a fluorine-18 atom.

3. The fluoroalkyl tetrabenazine compound according to claim 1, comprising a fluorine-19 atom.

4. The fluoroalkyl tetrabenazine compound according to claim 1, wherein —$OR^5$ is an ester moiety.

5. The fluoroalkyl tetrabenazine compound according to claim 1, which is enantiomerically enriched.

6. The enantiomerically enriched fluoroalkyl tetrabenazine compound according to claim 5 comprising a principal component enantiomer having structure II (II)

wherein $R^1$ is a $C_1$-$C_{10}$ fluorinated aliphatic radical; $R^2$ is a $C_1$-$C_{10}$ aliphatic radical; $R^3$ is hydrogen or a $C_1$-$C_{10}$ aliphatic radical; $R^4$ is hydrogen or a $C_1$-$C_{10}$ aliphatic radical; and $R^5$ is hydrogen, a $C_1$-$C_{10}$ aliphatic radical, a $C_2$-$C_{10}$ cycloaliphatic radical, or a $C_2$-$C_{20}$ aromatic radical.

7. The enantiomerically enriched fluoroalkyl tetrabenazine compound according to claim 6, which is at least 80% enantiomerically enriched.

8. The enantiomerically enriched fluoroalkyl tetrabenazine compound according to claim 5, comprising a fluorine-18 atom.

9. The enantiomerically enriched fluoroalkyl tetrabenazine compound according to claim 6, wherein —$OR^5$ is an ester moiety.

10. The enantiomerically enriched fluoroalkyl tetrabenazine compound according to claim 5 comprising a principal component enantiomer having structure III

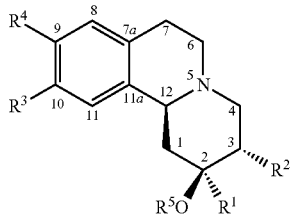

(III)

wherein $R^1$ is a $C_1$-$C_{10}$ fluorinated aliphatic radical; $R^2$ is a $C_1$-$C_{10}$ aliphatic radical; $R^3$ is hydrogen or a $C_1$-$C_{10}$ aliphatic radical; $R^4$ is hydrogen or a $C_1$-$C_{10}$ aliphatic radical; and $R^5$ is hydrogen, a $C_1$-$C_{10}$ aliphatic radical, a $C_2$-$C_{10}$ cycloaliphatic radical, or a $C_2$-$C_{20}$ aromatic radical.

11. The enantiomerically enriched fluoroalkyl tetrabenazine compound according to claim 10, wherein —$OR^5$ is an ester moiety.

12. A PET imaging agent comprising a fluoroalkyl tetrabenazine compound having structure I

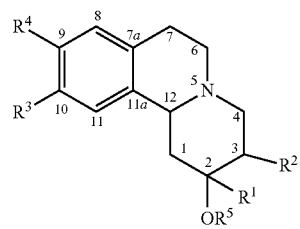

(I)

wherein $R^1$ is a $C_1$-$C_{10}$ fluorinated aliphatic radical comprising at least one fluorine-18 atom; $R^2$ is a $C_1$-$C_{10}$ aliphatic radical; $R^3$ is hydrogen or a $C_1$-$C_{10}$ aliphatic radical; $R^4$ is hydrogen or a $C_1$-$C_{10}$ aliphatic radical; and $R^5$ is hydrogen, a $C_1$-$C_{10}$ aliphatic radical, a $C_2$-$C_{10}$ cycloaliphatic radical, or a $C_2$-$C_{20}$ aromatic radical.

13. The PET imaging agent of claim 12 further comprising a salt of compound I.

14. The PET imaging agent of claim 12, wherein —$OR^5$ is an ester moiety.

15. A fluoroalkyl tetrabenazine carbinol compound having structure IV

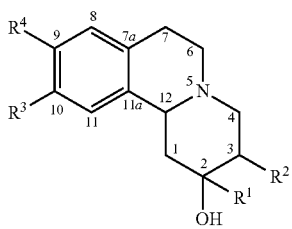

(IV)

wherein $R^1$ is a $C_1$-$C_{10}$ fluorinated aliphatic radical; $R^2$ is a $C_1$-$C_{10}$ aliphatic radical; $R^3$ is hydrogen or a $C_1$-$C_{10}$ aliphatic radical; and $R^4$ is hydrogen or a $C_1$-$C_{10}$ aliphatic radical.

16. The fluoroalkyl tetrabenazine carbinol compound according to claim 15, comprising a fluorine-18 atom.

17. The fluoroalkyl tetrabenazine carbinol compound according to claim 15, comprising a fluorine-19 atom.

18. The fluoroalkyl tetrabenazine carbinol compound according to claim 15, which comprises a mixture of diastereomers.

19. The fluoroalkyl tetrabenazine carbinol compound according to claim 15, which is enantiomerically enriched.

20. The enantiomerically enriched fluoroalkyl tetrabenazine carbinol compound according to claim 19 comprising a principal component enantiomer having structure V

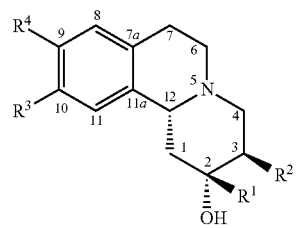

(V)

wherein $R^1$ is a $C_1$-$C_{10}$ fluorinated aliphatic radical; $R^2$ is a $C_1$-$C_{10}$ aliphatic radical; $R^3$ is hydrogen or a $C_1$-$C_{10}$ aliphatic radical; and $R^4$ is hydrogen or a $C_1$-$C_{10}$ aliphatic radical.

21. The enantiomerically enriched fluoroalkyl tetrabenazine carbinol compound according to claim 19 comprising a principal component enantiomer having structure VI

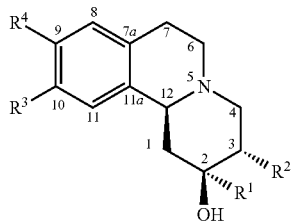

(VI)

wherein $R^1$ is a $C_1$-$C_{10}$ fluorinated aliphatic radical; $R^2$ is a $C_1$-$C_{10}$ aliphatic radical; $R^3$ is hydrogen or a $C_1$-$C_{10}$ aliphatic radical; and $R^4$ is hydrogen or a $C_1$-$C_{10}$ aliphatic radical.

22. The enantiomerically enriched fluoroalkyl tetrabenazine carbinol compound according to claim 19, comprising a fluorine-18 atom.

23. The enantiomerically enriched fluoroalkyl tetrabenazine carbinol compound according to claim 22, said compound being comprised in a formulation suitable for use in PET imaging.

24. A PET imaging agent comprising a fluoroalkyl tetrabenazine carbinol compound having structure IV

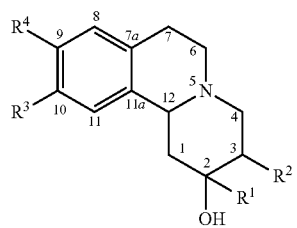
(IV)
wherein $R^1$ is a $C_1$-$C_{10}$ fluorinated aliphatic radical comprising at least one fluorine-18 atom; $R^2$ is a $C_1$-$C_{10}$ aliphatic radical; $R^3$ is hydrogen or a $C_1$-$C_{10}$ aliphatic radical; and $R^4$ is hydrogen or a $C_1$-$C_{10}$ aliphatic radical.
25. The PET imaging agent of claim 24 further comprising a salt of compound IV.
* * * * *